(12) United States Patent
Bradley et al.

(10) Patent No.: US 11,372,479 B2
(45) Date of Patent: Jun. 28, 2022

(54) MULTI-MODAL VISION ENHANCEMENT SYSTEM

(71) Applicant: Irisvision, Inc., Pleasanton, CA (US)

(72) Inventors: Chris Bradley, Baltimore, MD (US);
Bob Massof, Pasadena, MD (US);
Frank Werblin, Berkeley, CA (US)

(*) Notice: Subject to any disclaimer, the term of this patent is extended or adjusted under 35 U.S.C. 154(b) by 0 days.

(21) Appl. No.: 17/202,748

(22) Filed: Mar. 16, 2021

(65) Prior Publication Data
US 2021/0271318 A1    Sep. 2, 2021

Related U.S. Application Data

(63) Continuation-in-part of application No. 16/447,481, filed on Jun. 20, 2019, now Pat. No. 11,144,119,
(Continued)

(51) Int. Cl.
*G06F 3/01*   (2006.01)
*G02B 27/01*  (2006.01)
*H04N 5/77*   (2006.01)

(52) U.S. Cl.
CPC ........... *G06F 3/013* (2013.01); *G02B 27/017* (2013.01); *G02B 2027/014* (2013.01);
(Continued)

(58) Field of Classification Search
CPC .......... G02B 27/017; G02B 2027/0138; G02B 2027/014; G06F 3/013; G06F 2203/04805; H04N 5/772
See application file for complete search history.

(56) References Cited

U.S. PATENT DOCUMENTS

| 4,461,551 A | 7/1984 | Blaha |
| 4,586,892 A | 5/1986 | Ichizawa |

(Continued)

FOREIGN PATENT DOCUMENTS

| CN | 103110401 A | 5/2013 |
| CN | 104688179 A | 6/2015 |

(Continued)

OTHER PUBLICATIONS

International Search Report for PCT/US21/22491, dated Aug. 12, 2021.
(Continued)

*Primary Examiner* — Zaihan Jiang
(74) *Attorney, Agent, or Firm* — Novel IP

(57) ABSTRACT

A head-mounted video camera, a processor, and a display are integrated within the head-mounted device worn by the user. The head-mounted device is configured to capture images of the environment and subject those images to specialized processing in order to diagnose and/or make up for deficiencies in the user's eyesight. Different modes of operating the device are provided that enable the user to configure the device for a specific application. The modes of operation include at least an assistive mode, a diagnostic mode, and a therapeutic mode. Each mode of operation may include further options, where each option is dedicated to a specific processing approach specific to a condition that may afflict the user, ranging from contrast sensitivity issues to strabismus.

21 Claims, 26 Drawing Sheets

Related U.S. Application Data which is a continuation of application No. 16/137,003, filed on Sep. 20, 2018, now Pat. No. 10,444,833, which is a continuation of application No. 14/937,373, filed on Nov. 10, 2015, now Pat. No. 10,146,304, application No. 17/202,748, which is a continuation-in-part of application No. 17/084,233, filed on Oct. 29, 2020, which is a continuation of application No. 16/274,976, filed on Feb. 13, 2019, now Pat. No. 10,963,999, application No. 17/202,748, which is a continuation-in-part of application No. 16/503,098, filed on Jul. 3, 2019.

(60) Provisional application No. 62/990,422, filed on Mar. 16, 2020, provisional application No. 62/155,972, filed on May 1, 2015, provisional application No. 62/131,957, filed on Mar. 12, 2015, provisional application No. 62/077,434, filed on Nov. 10, 2014, provisional application No. 62/629,774, filed on Feb. 13, 2018, provisional application No. 62/694,173, filed on Jul. 5, 2018.

(52) U.S. Cl.
CPC ............... *G02B 2027/0138* (2013.01); *G06F 2203/04805* (2013.01); *H04N 5/772* (2013.01)

(56) References Cited

U.S. PATENT DOCUMENTS

| | | |
|---|---|---|
| 4,634,243 A | 1/1987 | Massof |
| 4,751,507 A | 6/1988 | Hama |
| 4,848,898 A | 7/1989 | Massof |
| 4,856,892 A | 8/1989 | Ben-Tovim |
| 5,151,722 A | 9/1992 | Massof |
| 5,359,675 A | 10/1994 | Siwoff |
| 5,717,834 A | 2/1998 | Werblin |
| 5,719,593 A | 2/1998 | De Lange |
| 5,808,589 A | 9/1998 | Fergason |
| 5,933,082 A | 8/1999 | Abita |
| 6,061,064 A | 5/2000 | Reichlen |
| 6,067,112 A | 5/2000 | Wellner |
| 6,529,331 B2 | 3/2003 | Massof |
| 6,545,685 B1 | 4/2003 | Dorbie |
| 6,590,583 B2 | 7/2003 | Soohoo |
| 6,591,008 B1 | 7/2003 | Surve |
| 6,704,034 B1 | 3/2004 | Rodriguez |
| 6,766,041 B2 | 7/2004 | Golden |
| 6,889,006 B2 | 5/2005 | Kobayashi |
| 7,486,302 B2 | 2/2009 | Shoemaker |
| 7,522,344 B1 | 4/2009 | Curatu |
| 7,542,210 B2 | 6/2009 | Chirieleison, Sr. |
| 7,612,804 B1 | 11/2009 | Marcu |
| 7,806,528 B2 | 10/2010 | Bedell |
| 7,883,210 B2 | 2/2011 | Filar |
| 8,103,352 B2 | 1/2012 | Fried |
| 8,239,031 B2 | 8/2012 | Fried |
| 8,253,787 B2 | 8/2012 | Yamamoto |
| 8,311,328 B2 | 11/2012 | Spruck |
| 8,350,898 B2 | 1/2013 | Chang |
| 8,454,166 B2 | 6/2013 | Fateh |
| 8,490,194 B2 | 7/2013 | Moskovitch |
| 8,511,820 B2 | 8/2013 | Trachtman |
| 8,516,584 B2 | 8/2013 | Moskovitch |
| 8,571,670 B2 | 10/2013 | Fried |
| 8,725,210 B2 | 5/2014 | Yang |
| 8,760,569 B2 | 6/2014 | Yang |
| 8,798,453 B2 | 8/2014 | Lawton |
| 8,836,778 B2 | 9/2014 | Ignatovich |
| 8,862,183 B2 | 10/2014 | Kulas |
| D717,856 S | 11/2014 | Slawson |
| 8,888,288 B2 | 11/2014 | Iravani |
| 8,905,543 B2 | 12/2014 | Davis |
| 8,922,366 B1 | 12/2014 | Frank |
| 8,976,247 B1 | 3/2015 | Karner |
| 9,019,420 B2 | 4/2015 | Hurst |
| 9,031,610 B2 | 5/2015 | Kulas |
| 9,066,683 B2 | 6/2015 | Zhou |
| 9,149,179 B2 | 10/2015 | Barnard |
| 9,213,185 B1 | 12/2015 | Starner |
| 9,215,977 B2 | 12/2015 | Kohn Bitran |
| 9,545,422 B2 | 1/2017 | Greenberg |
| 9,706,918 B2 | 7/2017 | Myung |
| 9,891,435 B2 | 2/2018 | Boger |
| 10,092,182 B2 | 10/2018 | Myung |
| 10,146,304 B2 | 12/2018 | Werblin |
| 10,188,294 B2 | 1/2019 | Myung |
| D848,420 S | 5/2019 | Boger |
| 10,345,591 B2 | 7/2019 | Samec |
| D863,300 S | 10/2019 | Boger |
| 10,444,833 B2 | 10/2019 | Werblin |
| 10,488,659 B2 | 11/2019 | Boger |
| 10,613,323 B1 | 4/2020 | Wheelwright |
| 10,743,761 B2 | 8/2020 | Myung |
| 2002/0101568 A1 | 8/2002 | Eberl |
| 2002/0181115 A1 | 12/2002 | Massof |
| 2003/0182394 A1 | 9/2003 | Ryngler |
| 2004/0136570 A1 | 7/2004 | Ullman |
| 2004/0208343 A1 | 10/2004 | Golden |
| 2005/0162512 A1 | 7/2005 | Seakins |
| 2005/0200707 A1 | 9/2005 | Yogesan |
| 2005/0237485 A1 | 10/2005 | Blum |
| 2005/0270484 A1 | 12/2005 | Maeda |
| 2006/0129207 A1 | 6/2006 | Fried |
| 2006/0167530 A1* | 7/2006 | Flaherty ............... A61B 5/24 |
| | | 607/62 |
| 2006/0282129 A1 | 12/2006 | Fried |
| 2006/0290712 A1 | 12/2006 | Hong |
| 2007/0106143 A1* | 5/2007 | Flaherty ............... A61N 1/0531 |
| | | 607/116 |
| 2007/0198941 A1 | 8/2007 | Baar |
| 2007/0235648 A1 | 10/2007 | Teich |
| 2007/0280677 A1 | 12/2007 | Drake |
| 2007/0294768 A1 | 12/2007 | Moskovitch |
| 2008/0106489 A1 | 5/2008 | Brown |
| 2008/0184371 A1 | 7/2008 | Moskovitch |
| 2008/0238947 A1 | 10/2008 | Keahey |
| 2008/0247620 A1 | 10/2008 | Lewis |
| 2008/0278821 A1 | 11/2008 | Rieger |
| 2009/0059364 A1 | 3/2009 | Brown |
| 2009/0062686 A1 | 3/2009 | Hyde |
| 2009/0322859 A1* | 12/2009 | Shelton ............... H04N 13/207 |
| | | 348/46 |
| 2010/0016730 A1* | 1/2010 | Tanaka ............... A61B 3/024 |
| | | 600/476 |
| 2010/0079356 A1 | 4/2010 | Hoellwarth |
| 2010/0283800 A1 | 11/2010 | Cragun |
| 2010/0328420 A1 | 12/2010 | Roman |
| 2011/0085138 A1 | 4/2011 | Filar |
| 2011/0102579 A1 | 5/2011 | Sung |
| 2011/0221656 A1* | 9/2011 | Haddick ............... H04N 5/2254 |
| | | 345/156 |
| 2011/0224145 A1 | 9/2011 | Greenberg |
| 2011/0241976 A1 | 10/2011 | Boger |
| 2011/0299036 A1 | 12/2011 | Goldenholz |
| 2012/0062840 A1 | 3/2012 | Ballou, Jr. |
| 2012/0176689 A1 | 7/2012 | Brown |
| 2012/0194550 A1 | 8/2012 | Osterhout |
| 2012/0212594 A1* | 8/2012 | Barnes ............... G06V 10/20 |
| | | 348/E7.085 |
| 2012/0229617 A1 | 9/2012 | Yates |
| 2012/0242678 A1 | 9/2012 | Border |
| 2012/0249797 A1* | 10/2012 | Haddick ............... G04G 21/04 |
| | | 701/491 |
| 2012/0262558 A1 | 10/2012 | Boger |
| 2012/0277826 A1 | 11/2012 | Fried |
| 2012/0316776 A1 | 12/2012 | Brown |
| 2012/0320340 A1 | 12/2012 | Coleman, III |
| 2013/0050273 A1 | 2/2013 | Fujimura |
| 2013/0083185 A1 | 4/2013 | Coleman, III |
| 2013/0110236 A1 | 5/2013 | Nirenberg |
| 2013/0127980 A1 | 5/2013 | Haddick |

(56) References Cited

U.S. PATENT DOCUMENTS

| | | | |
|---|---|---|---|
| 2013/0128364 A1 | 5/2013 | Wheeler | |
| 2013/0150123 A1 | 6/2013 | Kulas | |
| 2013/0242262 A1 | 9/2013 | Lewis | |
| 2013/0293840 A1 | 11/2013 | Bartels | |
| 2013/0300919 A1 | 11/2013 | Fletcher | |
| 2013/0329190 A1 | 12/2013 | Lewis | |
| 2014/0002792 A1 | 1/2014 | Filar | |
| 2014/0071547 A1 | 3/2014 | O'Neill | |
| 2014/0078594 A1 | 3/2014 | Springer | |
| 2014/0085603 A1 | 3/2014 | Su | |
| 2014/0098120 A1 | 4/2014 | Ritts | |
| 2014/0114208 A1 | 4/2014 | Smith | |
| 2014/0132932 A1 | 5/2014 | Jung | |
| 2014/0192022 A1* | 7/2014 | Yamamoto | G06F 3/0488 345/174 |
| 2014/0218193 A1 | 8/2014 | Huston | |
| 2014/0228668 A1 | 8/2014 | Wakizaka | |
| 2014/0268053 A1 | 9/2014 | Fabian | |
| 2014/0327753 A1 | 11/2014 | Prabhakar | |
| 2014/0327754 A1 | 11/2014 | Prabhakar | |
| 2014/0327755 A1 | 11/2014 | Prabhakar | |
| 2014/0350379 A1 | 11/2014 | Verdooner | |
| 2015/0002950 A1 | 1/2015 | O'Neill | |
| 2015/0042873 A1 | 2/2015 | Hunt | |
| 2015/0045012 A1 | 2/2015 | Siminou | |
| 2015/0077565 A1 | 3/2015 | Karner | |
| 2015/0098060 A1 | 4/2015 | Zhou | |
| 2015/0103317 A1* | 4/2015 | Goldfain | A61B 3/14 351/207 |
| 2015/0104087 A1 | 4/2015 | Katuwal | |
| 2015/0138048 A1 | 5/2015 | Park | |
| 2015/0169531 A1 | 6/2015 | Campbell | |
| 2015/0223678 A1 | 8/2015 | Goldfain | |
| 2015/0223686 A1 | 8/2015 | Wang | |
| 2015/0234189 A1* | 8/2015 | Lyons | G02B 27/017 345/174 |
| 2015/0254524 A1 | 9/2015 | Dickrell, III | |
| 2015/0257639 A1 | 9/2015 | Manquez Hatta | |
| 2015/0313462 A1 | 11/2015 | Reis | |
| 2015/0320313 A1 | 11/2015 | Stamile | |
| 2015/0339589 A1 | 11/2015 | Fisher | |
| 2015/0346348 A1 | 12/2015 | Liu | |
| 2015/0348327 A1* | 12/2015 | Zalewski | G06T 19/006 345/419 |
| 2016/0015264 A1 | 1/2016 | Pankajakshan | |
| 2016/0045388 A1 | 2/2016 | Krenik | |
| 2016/0048203 A1 | 2/2016 | Blum | |
| 2016/0051142 A1 | 2/2016 | Howes | |
| 2016/0063893 A1* | 3/2016 | Kanuganti | H04N 21/8545 348/62 |
| 2016/0097930 A1 | 4/2016 | Robbins | |
| 2016/0104453 A1 | 4/2016 | Borenstein | |
| 2016/0113489 A1 | 4/2016 | Myung | |
| 2016/0156850 A1 | 6/2016 | Werblin | |
| 2016/0173752 A1 | 6/2016 | Caviedes | |
| 2016/0264051 A1 | 9/2016 | Werblin | |
| 2016/0314564 A1 | 10/2016 | Jones | |
| 2016/0379593 A1 | 12/2016 | Borenstein | |
| 2017/0172675 A1 | 6/2017 | Jarc | |
| 2017/0200296 A1 | 7/2017 | Jones | |
| 2017/0236332 A1 | 8/2017 | Kipman | |
| 2017/0280996 A1 | 10/2017 | Myung | |
| 2018/0017820 A1 | 1/2018 | Cheng | |
| 2018/0116509 A1 | 5/2018 | Myung | |
| 2018/0125716 A1 | 5/2018 | Cho | |
| 2018/0144554 A1 | 5/2018 | Watola | |
| 2018/0239137 A1 | 8/2018 | Boger | |
| 2018/0239425 A1 | 8/2018 | Jang | |
| 2019/0056783 A1 | 2/2019 | Werblin | |
| 2019/0094552 A1 | 3/2019 | Shousha | |
| 2019/0180421 A1 | 6/2019 | Kim | |
| 2019/0208186 A1 | 7/2019 | Kawabe | |
| 2019/0222817 A1 | 7/2019 | Abou Shousha | |
| 2019/0251672 A1 | 8/2019 | Lim | |
| 2019/0251679 A1 | 8/2019 | Werblin | |
| 2019/0302886 A1 | 10/2019 | Werblin | |
| 2020/0008673 A1 | 1/2020 | Myung | |
| 2020/0112691 A1 | 4/2020 | Werblin | |
| 2021/0153741 A1* | 5/2021 | Berdahl | A61B 3/16 |
| 2021/0290056 A1 | 9/2021 | Karandikar | |

FOREIGN PATENT DOCUMENTS

| | | |
|---|---|---|
| EP | 2621169 A1 | 7/2013 |
| JP | 2004279733 A | 10/2004 |
| JP | 2005524462 A | 8/2005 |
| JP | 2006212102 A | 8/2006 |
| JP | 2007178409 | 7/2007 |
| JP | 2007520243 A | 7/2007 |
| JP | 2008093118 A | 4/2008 |
| JP | 2008295725 A | 12/2008 |
| JP | 2009031685 | 2/2009 |
| JP | 2013104986 A | 5/2013 |
| JP | 2013125038 | 6/2013 |
| WO | 1992008157 A1 | 5/1992 |
| WO | 1995006288 A2 | 3/1995 |
| WO | 1998044468 A1 | 10/1998 |
| WO | 2002086590 A1 | 10/2002 |
| WO | 2002099597 A2 | 12/2002 |
| WO | 03043363 A1 | 5/2003 |
| WO | 2007069294 A1 | 6/2007 |
| WO | 2008055262 A2 | 5/2008 |
| WO | 2011159757 A2 | 12/2011 |
| WO | 2012142202 A1 | 10/2012 |
| WO | 2012176960 A1 | 12/2012 |
| WO | 2014181096 A1 | 11/2014 |
| WO | 2014194182 A1 | 12/2014 |
| WO | 2015035229 A2 | 3/2015 |
| WO | 2015054672 A1 | 4/2015 |
| WO | 2015051779 A1 | 5/2015 |
| WO | 2016077343 A1 | 5/2016 |
| WO | 2016144419 A1 | 9/2016 |
| WO | 2016205709 A1 | 12/2016 |
| WO | 2018053509 A1 | 3/2018 |
| WO | 2019094047 A1 | 5/2019 |
| WO | 2019160962 A1 | 8/2019 |

OTHER PUBLICATIONS

Written Opinion of the International Searching Authority for PCT/US21/22491, dated Aug. 12, 2021.

Stelmack, et al. "Is there a standard of care for eccentric viewing training?" Journal of Rehabilitation Research & Development; vol. 41, No. 5, pp. 729-738; Sep./Oct. 2004.

Hassan, et al. "Changes in the Properties of the Preferred Retinal Locus with Eccentric Viewing Training", Optom Vis Sci 2019;96:79-86. doi: 10.1097/OPX.0000000000001324.

Web Search History for U.S. Appl. No. 16/447,481, filed Sep. 10, 2020.

Gergely Vass and Tama Perlaki; Applying and removing lens distortion in post production, Colorfront Ltd., Budapest, 2003.

Eric Kenneth Victorson; A Head Mounted Digital Image Warping Prosthesis for Age-Related Macular Degeneration; U of Minn., May 2014.

International Search Report for PCT/US15/59950, dated Apr. 11, 2016.

Written Opinion of the International Searching Authority for PCT/US15/59950, dated Apr. 11, 2016.

Chen-Yung Hsu and Mark M. Uslan; When Is a Little Magnification Enough? A Review of Microsoft Magnifier, AccessWorld Magazine, Jul. 2000, vol. 1, No. 4.

Richard D. Juday and David S. Loshin; Some Examples of Image Warping for Low Vision Prosthesis; Speidigitallibrary.org, Aug. 22, 1988.

Google Search of How to Install and Use Microsoft Magnifier, Mar. 29, 2018.

International Search Report for PCT/US16/12135, dated Apr. 29, 2016.

(56) References Cited

OTHER PUBLICATIONS

Written Opinion of the International Searching Authority for PCT/US16/12135, dated Apr. 29, 2016.
International Search Report for PCT/US20/40726, dated Sep. 14, 2020.
Written Opinion of the International Searching Authority for PCT/US20/40726, dated Sep. 14, 2020.
International Search Report for PCT/US19/17860, dated May 14, 2019.
Written Opinion of the International Searching Authority for PCT/US19/17860, dated May 14, 2019.
Sample et al.; "Imaging and Perimtery Society Standards and Guidelines" Optometry and Vision Science, vol. 88, No. 1, Jan. 2011, pp. 4-7.
Haddock et al.; Simple, inexpensive technique for high-quality smartphone fundus photography in human and animal eyes; Journal of Opththalmology; 2013; pp. 1-5; published online Sep. 19, 2013.
Hester et al.; Smart Phoneography—how to take slit lamp photographs with an iphone; 12 pages; retrieved from internet (http://eyewiki.aao.org/Smart_Phoneography_-_How_to_take_slit_lamp_photographs_with_an_iPhone).
Github; RNCryptor/RNCryptor; 7 pages; retrieved from the internet (https://github.com/RNCryptor/RNCryptor).
Kim et al.; Smartphone photography safety; Ophthalmology; 119(10); pp. 220-2201; Oct. 2012.
Lord et al.; Novel uses of smartphones in ophthalmology; Ophthalmology; 117(6); pp. 1274-1274 e3; Jun. 2010.
Teichman et al.; From iphone to eyephone: a technique for photodocumentation; Can. J. Ophthalmol.; 46(3); pp. 284-286; Jun. 2011.
Wikipedia: Soap note; 6 pages; retreived from the interet (http://en.wikipedia.org/wiki/SOAP_note).
Apple Developer; Apple app store connect user guide; 4 pages; retrieved from the internet (https://developer.apple.com/support/ap-store-connect/).
Bastawrous; Smartphone fundoscopy; Ophthalmology; 119(2); pp. 432-433. e2; Feb. 2012.
Chakrabarti; Application of mobile technology in ophthalmology to meet the demands of low-resource settings; Journal of Mobile Technology in Medicine; 1(4S); pp. 1-3; Dec. 2012.
Chhablani et al.; Smartphones in ophthalmology; Indian J. Ophthalmol.; 60(2); pp. 127-131; Mar./Apr. 2012 (Author Manuscript).
Echanique et al.; Ocular Cellscope; University of California at Berkeley; Electrical engineering and computer sciences; 23 pages; retrieved from the internet (http://digitalassets.lib.berkeley.edu/techreports/ucb/text/EECS-2014-91.pdf); May 16, 2014.
Github; Nicklockwood/iCarousel; A simple, highly customisable, data-driven 3D carousel for iOS and Mac OS; 30 pages; retrieved from teh internet (https://github.com/nicklockwood/iCarousel).
Github; Project-imas / encrypted-core-data; 6 pages; retrieved from the internet (https://github.com/project-imas/encrypted-core-data).
International Search Report for PCT/US16/38176, dated Sep. 7, 2016.

* cited by examiner

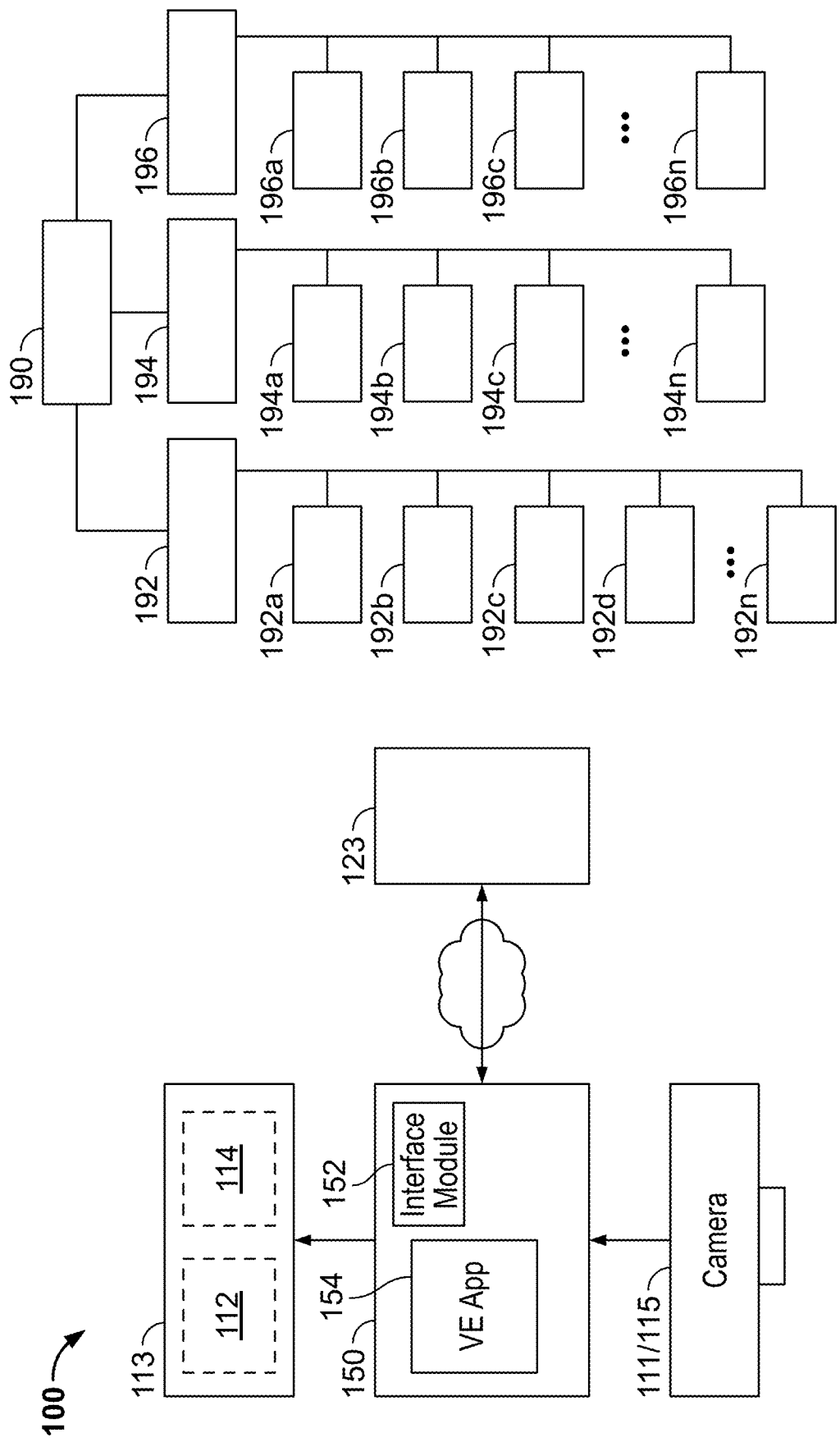

| Row | RABIN CONTRAST SENSITIVITY TEST<br>DEVELOPED BY JEFF RABIN, O.D., Ph.D.<br>LTC U.S. ARMY (RET.)<br>FOR TESTING AT 4 METERS (13 FEET)<br>LETTER SIZE 20M, 4/20, 13/66 (6/30, 20/100 EQUIV.) | | | log CS |
|---|---|---|---|---|
| 1 | Z | R | K | D | C | 0.25 |
| 2 | D | N | C | H | V | 0.50 |
| 3 | C | D | H | N | R | 0.75 |
| 4 | R | V | Z | O | S | 1.00 |
| 5 | O | S | D | V | N | 1.25 |
| 6 | N | O | Z | C | D | 1.50 |
| 7 | R | D | N | S | K | 1.75 |
| 8 | O | K | S | V | Z | 2.00 |

FIG. 8A

MULTI-MODAL VISION ENHANCEMENT SYSTEM

CROSS-REFERENCE

The present application relies on, for priority, U.S. Patent Provisional Application No. 62/990,422, titled "Multi-Modal Vision Enhancement System" and filed on Mar. 16, 2020, which is herein incorporated by reference in its entirety.

The present application is also a continuation-in-part application of U.S. patent application Ser. No. 16/447,481, titled "Methods and Apparatus for Vision Enhancement" and filed on Jun. 20, 2019, which is a continuation application of U.S. patent application Ser. No. 16/137,003, of the same title, filed on Sep. 20, 2018, and issued as U.S. Pat. No. 10,444,833 on Oct. 15, 2019, which is a continuation application of U.S. patent application Ser. No. 14/937,373, of the same title, filed on Nov. 10, 2015, and issued as U.S. Pat. No. 10,146,304 on Dec. 4, 2018, which, in turn, relies on the following for priority: U.S. Patent Provisional Application No. 62/077,434, titled "Low Vision Head-Mounted Visual Enhancement Device" and filed on Nov. 10, 2014; U.S. Patent Provisional Application No. 62/131,957, titled "Eye Tracking Systems" and filed on Mar. 12, 2015; and U.S. Patent Provisional Application No. 62/155,972, titled "Universal Testbed and Platform to Improve the Performance of Low Vision Patients" and filed on May 1, 2015. All of the above-mentioned applications are herein incorporated by reference in their entirety.

The present application is also a continuation-in-part application of U.S. patent application Ser. No. 17/084,233, titled "Methods and Apparatus for Contrast Sensitivity Compensation" and filed on Oct. 29, 2020, which is a continuation application of U.S. patent application Ser. No. 16/274,976, of the same title and filed on Feb. 13, 2019, which, in turn, relies on U.S. Patent Provisional Application No. 62/629,774, titled "Methods and Apparatus for Low Vision Enhancement" and filed on Feb. 13, 2018, for priority. All of the above-mentioned applications are herein incorporated by reference in their entirety.

The present application is also a continuation-in-part application of U.S. patent application Ser. No. 16/503,098, titled "Methods and Apparatuses for Compensating for Retinitis Pigmentosa" and filed on Jul. 3, 2019, which, in turn, relies on U.S. Patent Provisional Application No. 62/694,173, titled "Compensating for Retinitis Pigmentosa: Using dynamic shifts in field of view and magnification" and filed on Jul. 5, 2018, for priority. All of the above-mentioned applications are herein incorporated by reference in their entirety.

FIELD

The present specification relates to vision-enhancement systems and methods. Specifically, the embodiments disclosed herein are directed to a head-mounted system with at least one software platform that integrates a multitude of vision enhancement modes to tailor generated visual images to a variety of different types of vision-related conditions.

BACKGROUND

The human visual system can suffer from a multitude of conditions that conventional glasses are unable to address. For example, individuals with retinitis pigmentosa experience a progressive loss of the visual field, which is the area of space visible at a given point in time without moving the eyes and, as a result, may have a loss of peripheral vision, or "tunnel vision". Others may experience holes in their visual fields, referred to as scotoma, or suffer from an inability to properly assess contrast in visual images because they have lost the ability to visually process certain spectral frequencies. Still others may suffer from strabismus where a patient is unable to physically and simultaneously align both eyes on a common target, also known as being cross-eyed.

Additionally, as previously disclosed in a parent application to the present specification, the human visual system may also suffer from conditions that may only be addressed by providing the patient with control over the degree of magnification applied to delivered visual images. A significant portion of the population suffers from low vision, those with visual acuity of 20/80 or worse. As with the above-described conditions, low vision greatly diminishes a person's quality of life, greatly limiting his or her ability to socialize, shop, cook, and travel. Recent technical advances in digital technology have greatly improved the ability to read with large magnified CCTV displays, but mobility still remains a difficult challenge: magnification is effective for static activities like reading or watching TV, but does not enable a person to move through the environment while viewing a magnified view of the environment because magnification of the entire image dramatically reduces the overall field of view. Thus, for instance, if a person with normal vision has a visual field of view of 180 degrees, a system that magnifies by 6 times reduces that field of view to 30 degrees, thus eliminating a person's peripheral vision.

Corrective systems that attempt to address any of the aforementioned conditions may be ineffective, however, they fail to tailor delivered visual images to one or more patient-specific variables. For example, if the delivered visual images are not properly tailored to the patient's specific degree of eye separation, referred to as interpupillary distance, the images may appear offset, leading to eye strain. If a degree of magnification of delivered visual images are not properly tailored to the patient's specific degree or extent of magnification need, it may lead to the loss of peripheral vision at the wrong time.

Given the plethora of varied vision-related conditions and the potential ineffectiveness of a fixed, hardwired or non-customizable approach to solving highly variable vision conditions, it is important for a treatment system to have a number of integrated assistive, diagnostic, and therapeutic modes of operation. Existing solutions, however, tend to provide fixed applications. For example, U.S. Pat. No. 10,444,833, titled 'Methods and apparatus for vision enhancement', assigned to the Applicant, discloses a "portable user vision-enhancement system comprising: a memory including a stored program; a camera mounted to view a scene in front of a user and operable to obtain input video images of a scene; a processor programmed to execute the stored program to transform the input video images of the scene into a stream of output video images of the scene wherein each output video image has a magnification bubble that enlarges a portion of the output video image of the scene within a peripheral portion of the scene; wherein the magnification bubble has variable attributes where the processor is programmed to vary attributes of the magnification bubble including at least one of the position of the magnification bubble, a size of the magnification bubble, a shape of the magnification bubble, and a magnification power of the magnification bubble, in the scene in the stream of output video images in response to an input signal; and a digital display disposed to be viewed by the user that displays the output video images."

There is a further need for methods and systems that enable enhanced representation of the visual world, and that also enable mobility for navigation and recognition, and which are adapted to different types of applications. There is also a need for an integrated platform that can address a multitude of different vision-related conditions and wherein the extent, scope and/or nature of modification of the visual images presented to a patient may be tailored to the patient's specific requirement, or may be under the control of the patient within certain predefined boundaries.

SUMMARY

The following embodiments and aspects thereof are described and illustrated in conjunction with systems, tools and methods, which are meant to be exemplary and illustrative, not limiting in scope. The present application discloses numerous embodiments.

The present specification discloses a computer readable program adapted to be executed in a portable user vision enhancement and/or assessment system configured in a form of a housing adapted to fit onto a user's head and comprising a memory physically coupled to the housing, a display physically coupled to the housing, a camera physically coupled to the housing, adapted to view a scene in front of the user, and configured to obtain input video images of the scene, and at least one processor physically coupled to the housing and in data communication with the memory, display, and camera, wherein the computer readable program comprises a plurality of programmatic instructions that, when executed by the at least one processor: generates data representative of a first graphical user interface; and causes said data to be transmitted to the display, wherein, when displayed on the display, the first graphical user interface comprises: a first option that, when actuated by the user, causes the plurality of programmatic instructions to generate a plurality of assistive operational modes; a second option that, when actuated by the user, causes the plurality of programmatic instructions to generate a plurality of therapeutic operational modes; and a third option that, when actuated by the user, causes the plurality of programmatic instructions to generate a plurality of diagnostic modes, wherein the plurality of programmatic instructions, when executed by the at least one processor, is further configured to receive a selection from the user, via the display, of one of the assistive operational modes, therapeutic operational modes, or diagnostic operational modes, to access a portion of the plurality of programmatic instructions associated with the selection, and to execute the portion of the plurality of programmatic instructions associated with the selection.

Optionally, when executed by the at least one processor, the plurality of programmatic instructions is further adapted to concurrently present the first option, the second option, and the third option in the first graphical user interface.

Optionally, the plurality of assistive operational modes comprises at least one of a magnification mode, a magnification mode with a customizable bubble, a retinitis pigmentosa mode, or a contrast sensitivity mode and wherein each of the plurality of assistive operational modes is concurrently displayed in a same graphical user interface.

Optionally, the plurality of diagnostic operational modes comprises at least one of an interpupillary distance mode or a visual field measurement mode wherein each of the plurality of diagnostic operational modes is concurrently displayed in a same graphical user interface.

Optionally, the plurality of therapeutic operational modes comprises a strabismus treatment mode.

Optionally, upon the first option being actuated by the user, the plurality of programmatic instructions is further adapted to generate data representative of a second graphical user interface and transmit said data representative of the second graphical user interface to the display wherein, when displayed on the display, the second graphical user interface displays at least one of a magnification mode option, a magnification with a bubble mode option, a retinitis pigmentosa mode option or a contrast sensitivity mode option.

Optionally, upon the retinitis pigmentosa mode option being selected by the user, the plurality of programmatic instructions is further adapted to access a portion of the plurality of programmatic instructions associated with the retinitis pigmentosa mode wherein, upon executing the portion of the plurality of programmatic instructions associated with the retinitis pigmentosa mode, the plurality of programmatic instructions is further adapted to access images of the scene encompassing a first field of view and minimize all content in said images to fit within a second field of view that is smaller than the first field of view. Optionally, upon the contrast sensitivity mode option being selected by the user, the plurality of programmatic instructions is further adapted to access a portion of the plurality of programmatic instructions associated with the contrast sensitivity mode wherein, upon executing the portion of the plurality of programmatic instructions associated with the contrast sensitivity mode, the plurality of programmatic instructions is further adapted to access images of the scene and processes the images to preferentially enhance the images at a spatial frequency Cp, where Cp is the maximum spatial frequency at which a user can discern contrast. Optionally, upon the contrast sensitivity mode option being selected by the user, the plurality of programmatic instructions is further adapted to access a portion of the plurality of programmatic instructions associated with the contrast sensitivity mode wherein, upon executing the portion of the plurality of programmatic instructions associated with the contrast sensitivity mode, the plurality of programmatic instructions is further adapted to acquires images of the scene, access stored frequencies indicative of the user's contrast sensitivity, and adjust frequencies of the images of the scene based upon the stored frequencies, and generate images having adjusted frequencies for display. Optionally, upon the magnification mode option being selected by the user, the plurality of programmatic instructions is further adapted to access a portion of the plurality of programmatic instructions associated with the magnification mode wherein, upon executing the portion of the plurality of programmatic instructions associated with the magnification mode, the plurality of programmatic instructions is further adapted to access images of the scene and process the images to generate a magnification region in the images, wherein the magnification region has a magnification level that has a higher magnification level near a center of the magnification region and a lower magnification level near an edge of the magnification region. Optionally, the plurality of programmatic instructions is further adapted to access a portion of the plurality of programmatic instructions associated with the contrast sensitivity mode wherein, upon executing the portion of the plurality of programmatic instructions associated with the contrast sensitivity mode, the plurality of programmatic instructions is further adapted to determine frequencies within a spatial range at which the user experiences contrast sensitivity and is configured to adjust one or more of the images to compensate for the determined frequencies.

Optionally, upon the second option being actuated by the user, the plurality of programmatic instructions is further adapted to generate data representative of a second graphical user interface and transmit said data representative of the second graphical user interface to the display wherein, when displayed on the display, the second graphical user interface displays at least one of an interpupillary distance mode or a visual field measurement mode. Optionally, upon the interpupillary distance mode option being selected by the user, the plurality of programmatic instructions is further adapted to access a portion of the plurality of programmatic instructions associated with the interpupillary distance mode wherein, upon executing the portion of the plurality of programmatic instructions associated with the interpupillary distance mode, the plurality of programmatic instructions is further adapted to generate a vertical line and a horizontal line perpendicular to the horizontal line and, in response to a user input, move the vertical line along a length of the horizontal line. Optionally, upon the visual field measurement mode option being selected by the user, the plurality of programmatic instructions is further adapted to access a portion of the plurality of programmatic instructions associated with the visual field measurement mode wherein, upon executing the portion of the plurality of programmatic instructions associated with the visual field measurement mode, the plurality of programmatic instructions is further adapted to a) generate, and cause a display of, a sequence of targets to the user, b), record data representative of the user having seen a first of the targets in response to the user's input, cause the first of the targets to disappear and cause a display of a second of the targets, c) continue to display each of the targets for a predefined period of time in an absence of the user's input and record a lack of response, with the predefined period of time, from the user, and d) generate data representative of the user's visual field and indicative of where, within the user's visual field, the user is unable to see based on b and c.

Optionally, upon the third option being actuated by the user, the plurality of programmatic instructions is further adapted to generate data representative of a second graphical user interface and transmit said data representative of the second graphical user interface to the display wherein, when displayed on the display, the second graphical user interface displays a strabismus treatment mode. Optionally, upon the strabismus treatment mode option being selected by the user, the plurality of programmatic instructions is further adapted to access a portion of the plurality of programmatic instructions associated with the strabismus treatment mode wherein, upon executing the portion of the plurality of programmatic instructions associated with the strabismus treatment mode, the plurality of programmatic instructions is further adapted to position a first image along a first visual axis associated with the user's right eye and position a second image along a second visual axis associated with the user's left eye and, over a predefined period of time, move the first image relative to the second image. Optionally, upon the strabismus treatment mode option being selected by the user, the plurality of programmatic instructions is further adapted to access a portion of the plurality of programmatic instructions associated with the strabismus treatment mode wherein, upon executing the portion of the plurality of programmatic instructions associated with the strabismus treatment mode, the plurality of programmatic instructions is further adapted to continue to position the first image along the first visual axis relative to the second image along the second visual axis until the first visual axis is parallel to the second visual axis. Optionally, upon the strabismus treatment mode option being selected by the user, the plurality of programmatic instructions is further adapted to access a portion of the plurality of programmatic instructions associated with the strabismus treatment mode wherein, upon executing the portion of the plurality of programmatic instructions associated with the strabismus treatment mode, the plurality of programmatic instructions is further adapted to continue to position the first image along the first visual axis relative to the second image along the second visual axis until the first visual axis is offset from a center point of the user's field of view by a first amount and the second visual axis is offset from the center point of the user's field of view by a second amount, wherein the first amount is equal to the second amount. Optionally, the period of time ranges from one week to one year.

Optionally, the computer readable program is adapted to be executed in a mobile phone wherein the display, camera, and at least one processor is positioned in the mobile phone.

Optionally, the computer readable program is adapted to be executed in a virtual reality headset and wherein the display, camera, and at least one processor is positioned in the virtual reality headset.

The present specification also discloses a portable user vision-enhancement system comprising: a memory including a stored program; a camera mounted to view a scene in front of a user and operable to obtain input video images of a scene; a processor programmed to recognize a need of a user using the portable vision-enhancement system, and execute a stored program to transform the input video images of the scene into a stream of output video images of the scene according to the recognized need of the user; and a digital display disposed to be viewed by the user that displays the output video images.

Optionally, the processor is in communication with an interface configured to receive input from the user, to specify the need of the user.

Optionally, the need of the user is at least one of an assistance, a diagnosis, and a therapy.

Optionally, the processor is programmed to execute the stored program to transform the input video images of the scene into stream of output video images of the scene wherein each output video image has a magnification bubble that enlarges a portion of the output video image of the scene within a peripheral portion of the scene and the magnification bubble has variable attributes where the processor is programmed to vary attributes of the magnification bubble including at least one of the position of the magnification bubble, a size of the magnification bubble, a shape of the magnification bubble, and a magnification power of the magnification bubble, in the scene in the stream of output video images in response to an input signal.

Optionally, the processor is programmed to execute the stored program to transform the input video images of the scene into stream of output video images of the scene that include a magnification bubble that overlays and enlarges a user-selected portion of the output video images of the scene within the context of the scene and the magnification bubble has variable attributes where the processor is programmed to vary attributes of the magnification bubble including at least one of the position of the magnification bubble, the size of the magnification bubble, the shape of the magnification bubble, and the magnification power of the magnification bubble, in the scene in the stream of output video images in response to an input signal.

Optionally, the further comprises a pair of goggles and an electronic device attached to the goggles, where said camera, the processor, and the screen are components of the electronic device where the electronic device is removably attached to the goggles. The electronic device may be a smartphone.

Optionally, the processor is configured to determine frequencies within a spatial range at which the user experiences contrast sensitivity, and use the determined frequencies to compensate for the contrast sensitivity.

Optionally, the processor is configured for measuring a visual field of the user by: presenting a random sequence of points, one point at a time, on the digital display; accepting an input from the user, the input indicating visibility of each point in the random sequence of points; and determining one or more areas in the user's visual field where vision is compromised, based on the input.

The present specification also discloses a portable user vision-enhancement system comprising: a memory including a stored program; a camera mounted to view a scene in front of a user and operable to obtain input video images of a scene; a processor programmed to execute the stored program to transform the input video images of the scene into a stream of output video images of the scene, wherein when the stored program is executed by the processor the input video images are compensated for a determined loss of frequencies within a spatial range of the user; and a digital display disposed to be viewed by the user that displays the output video images.

Optionally, the system further comprises the digital display presenting at least one image to the user to assess the user's contrast sensitivity.

Optionally, the system further comprises the processor determining frequencies at which the user experiences an unacceptable level of contrast perception, relative to how a person with normal vision would process the at least one image. Optionally, the system further comprises a user-operable controller for generating an input to the processor by which the user communicates the unacceptable level of contrast perception to the processor. Optionally, the processor is configured to determine the user's contrast sensitivity during an initial setup of the portable user vision-enhancement system.

Optionally, the system further comprises a user-operable controller for generating an input to the processor by which the magnification of the output video images is adjusted, wherein when the stored program is executed by the processor and the user operates the controller, the user adjusts the magnification of the output video images within the adjusted size of the output video images.

Optionally, the system further comprises a pair of goggles and an electronic device attached to the goggles, where the camera, the processor, and the screen are components of the electronic device. Optionally, said electronic device is removably attached to said goggles. The electronic device may be a smartphone.

The present specification also discloses a method for compensating for contrast sensitivity of a user, the method comprising: displaying at least one image to the user; receiving input from the user, the input indicating a set of frequencies within the user's spatial range where the user experiences an unacceptable level of contrast perception; adjusting images from a scene in front of a user based on the set of frequencies to compensate for the user's contrast sensitivity; and displaying the adjusted images from the scene to the user.

Optionally, the method further comprises accepting an input from the user to adjust magnification of the images from the scene.

The aforementioned and other embodiments of the present specification shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings:

FIG. 1E illustrates a block drawing of the components of an exemplary system of FIG. 1A, in accordance with some embodiments of the present specification;

FIG. 1F illustrates a functional diagram illustrating a relationship of the functional modules of the integrated vision-enhancement software platform, in accordance with some embodiments of the present specification;

FIG. 8A illustrates a typical contrast sensitivity chart that may be used to measure contrast sensitivity of a user to see contrasting images at different contrasts and different spatial frequencies, and therefore determine the spatial frequencies where the user experiences contrast sensitivity;

DETAILED DESCRIPTION

Figure 1A:
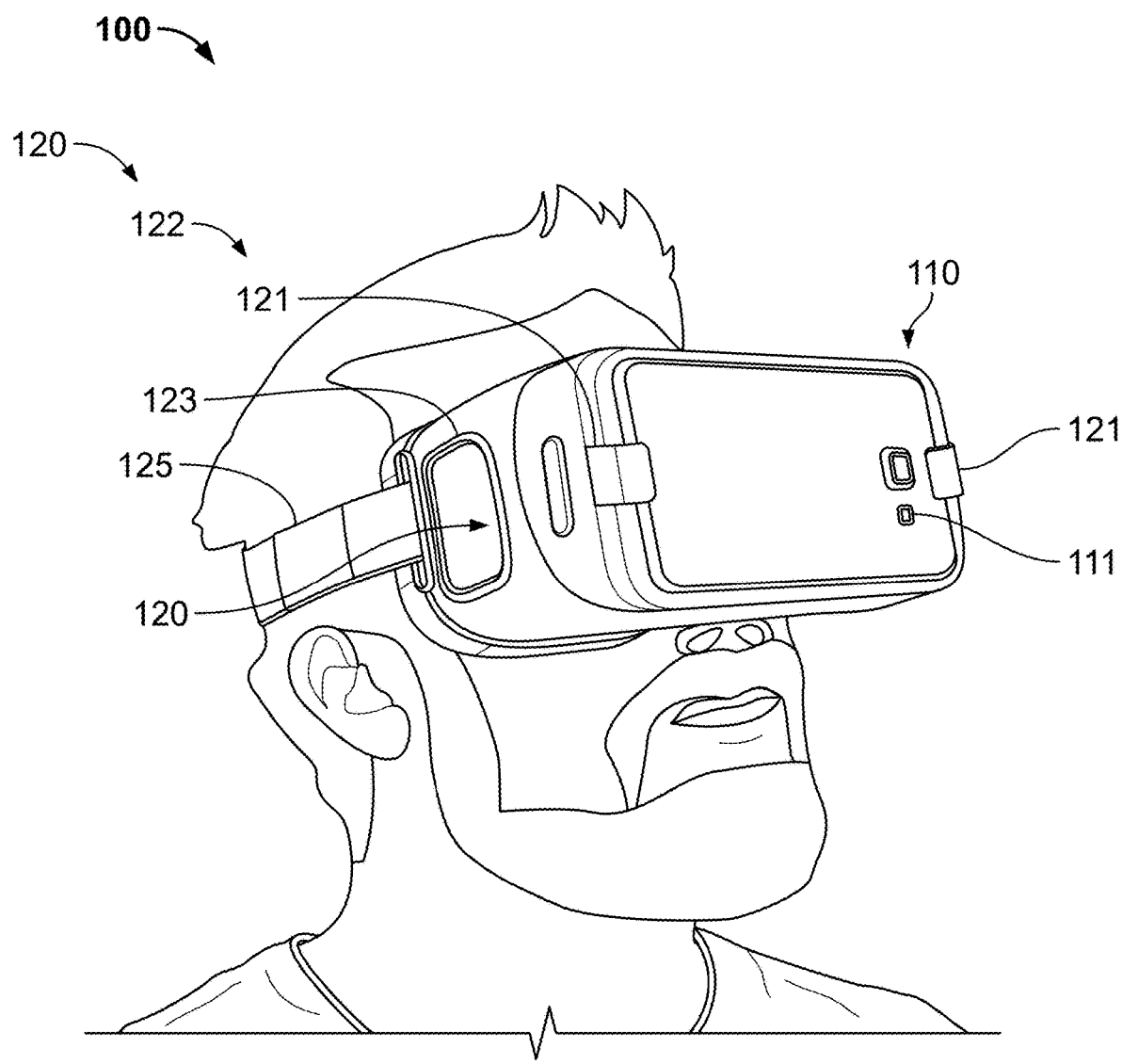
FIG. 1A illustrates an exemplary embodiment of a user-controllable vision-enhancement system on a user, in accordance with some embodiments of the present specification.

Embodiments of the present specification provide systems and methods for vision enhancement. A head-mounted video camera, a processor, and a display, are integrated within the head-mounted device worn by the user. The head-mounted device is configured to capture images of the environment and subject those images to specialized processing in order to diagnose and/or make up for deficiencies in the user's eyesight. In embodiments, different modes of operating the device are provided that enable the user to configure the device for a specific application. In some embodiments, the modes of operation include at least an assistive mode, a diagnostic mode, and a therapeutic mode. Each mode of operation may include further options, where each option is dedicated to a specific processing approach, specific to an issue that the user may be facing.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

In various embodiments, the vision enhancement system includes at least one processor capable of processing programmatic instructions, has a memory capable of storing programmatic instructions, and employs software comprised of a plurality of programmatic instructions for performing the processes described herein. In various embodiments, a computing device such as, but not limited to a mobile phone, may be employed to receive and process data signals and image data and may include an input/output controller, at least one communication interface and a system memory. The system memory includes at least one random access memory (RAM) and at least one read-only memory (ROM). These elements are in communication with a central processing unit (CPU) to enable operation of the computing device.

In various embodiments, the computing device may be a conventional standalone computer, or a mobile phone or alternatively, the functions of the computing device may be distributed across a network of multiple computer systems or mobile phones. In some embodiments, execution of a plurality of sequences of programmatic instructions or code, which are stored in one or more non-volatile memories, enable or cause the CPU of the computing device to perform or enable various functions, processes and algorithms, such as, for example, performing image reconstruction for display on a screen. In alternate embodiments, hard-wired circuitry may be used in place of, or in combination with, software instructions for implementation of the processes of systems and methods described in this application. Thus, the systems and methods described are not limited to any specific combination of hardware and software.

In some embodiments, the method of present specification is provided in the form of a computer program, comprising a plurality of programmatic instructions, that is adapted to be stored and executed in a variety of different mobile phones executing different operating systems and a variety of different virtual reality systems executing different operating systems; wherein said mobile phones and virtual reality systems comprise at least a processor, a camera and a display system. In embodiments, the method of present specification is provided in the form of a computer program, comprising a plurality of programmatic instructions, that is adapted to be stored and executed in a virtual reality headset and wherein a display, a camera, and at least one processor is positioned in the virtual reality headset.

Figure 1B:
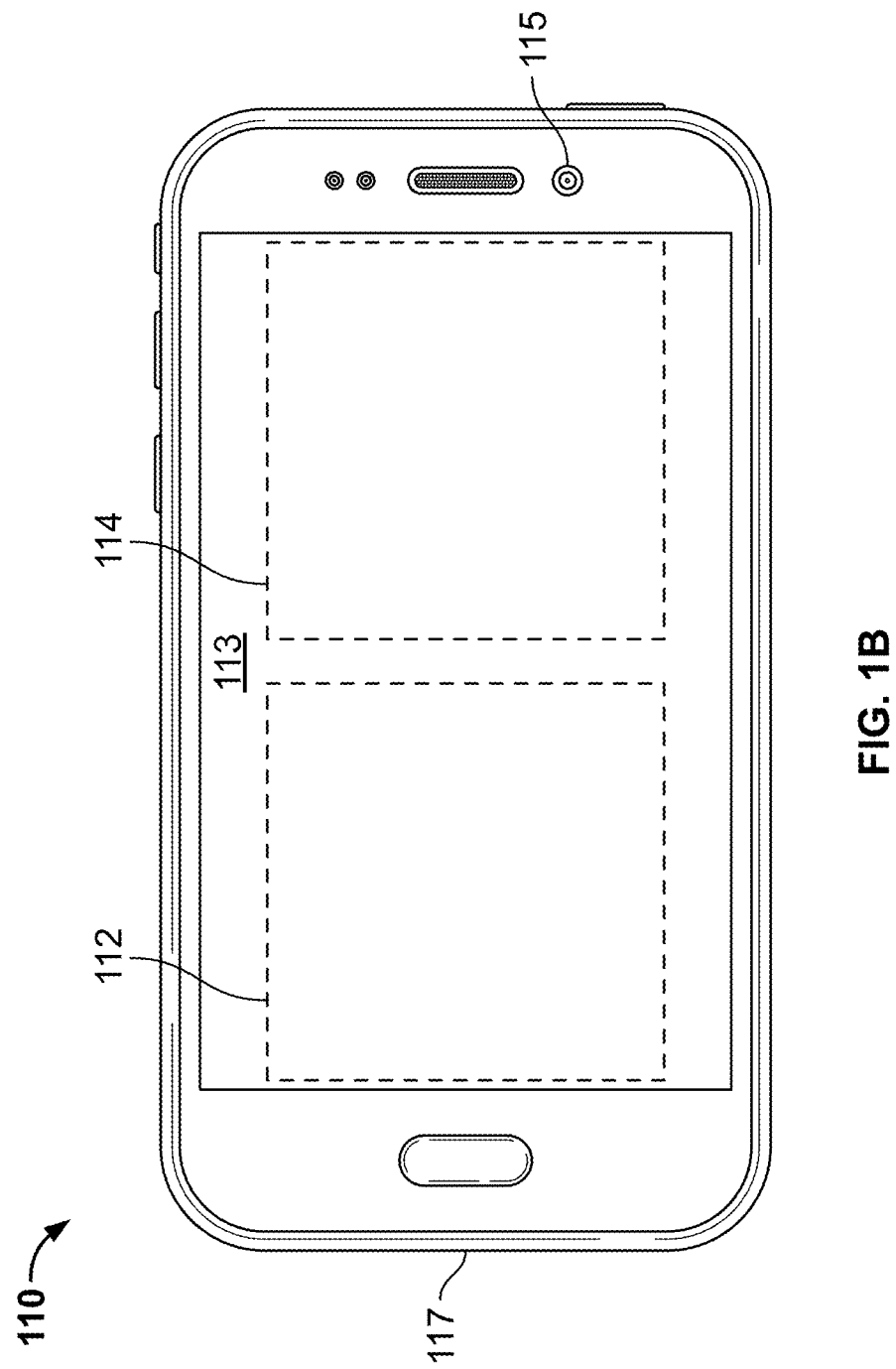
FIG. 1B illustrates a smartphone that may be used in the system of FIG. 1A, in accordance with some embodiments of the present specification.
Figure 1C:
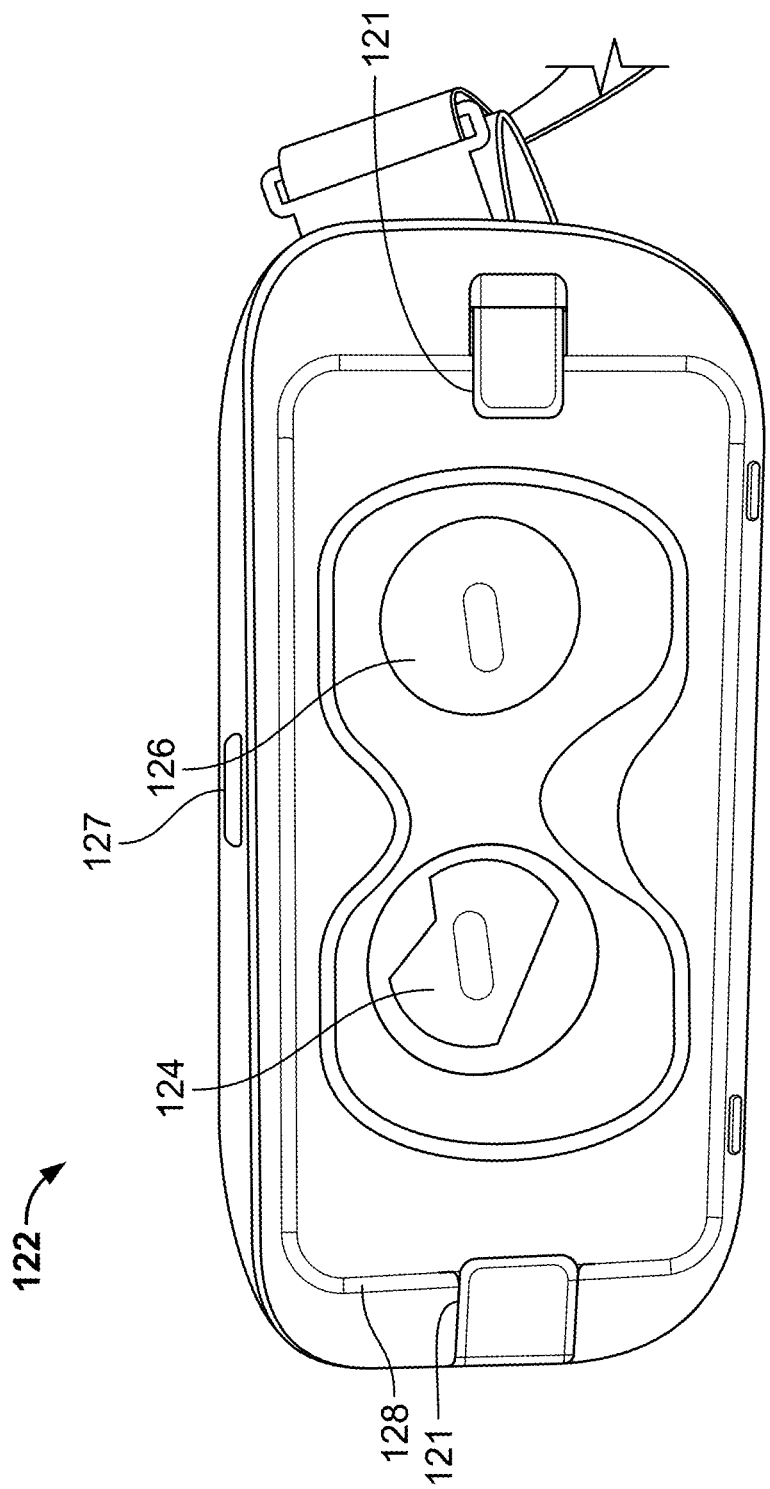
FIG. 1C illustrates body of a goggle that may be used in the system of FIG. 1A, in accordance with some embodiments of the present specification.

By way of a specific embodiment, FIGS. 1A, 1B, and 1C show a first embodiment user-controllable vision-enhancement system 100, where FIG. 1A shows the system being used by a user, FIG. 1B shows a smartphone used in the system and FIG. 1C shows the body of a head mounted device of the system. System 100 comprises a smartphone 110 and pair of goggles 120. Smartphone 110 comprises the electronics necessary for the vision-enhancement system 100, such as a processor and memory (not shown), a forward facing camera 111, as shown in FIG. 1A, and a screen 113 on the side opposite of the camera 111, as shown in FIG. 1B. In an embodiment, smartphone 110 also comprises an electrical connector 117 and may also include a backward facing camera 115, which may be used in certain embodiments. As described subsequently, processed camera images are displayed on a first portion of screen 113 shown as a left area 112 and a second portion of the screen is shown as right area 114. Smartphone 110 may further comprise a plurality of programmatic instructions which, when executed, implement one or more of the functional modules described herein and shown in, among other places, FIG. 1F.

Goggles 120 comprise a body 122 and a strap 125 for holding the goggles on the user's head and a connector 128 that mates with smartphone connector 117. Body 122 comprises, as shown in FIG. 1A, a pair of clamps 121 for removably restraining smartphone 110 and making the electrical connection between connectors 117 and 128, and input device 123 for providing input to the smartphone through the connectors and, as shown in FIG. 1C, a left lens 124 and right lens 126 and a focusing wheel 127. When assembled as in FIG. 1A, with smartphone 110 held in place by clamps 121, system 100 presents what is displayed in area 112 of screen 113, through lens 124, to the user's left eye, and what is displayed in area 114 of the screen, through lens 126, to the user's right eye. The user may use focusing wheel 127 to adjust the focus. In certain embodiments, goggles 120 are adapted to accept user input from input device 123, which may control or otherwise provide inputs to the accepted smartphone 110.

In embodiments, smartphone 110 is provided with programming, as through a vision-enhancement application (referred to herein as a "VE App") which can: operate camera 111 in a video mode to capture a stream of "input images"; perform image processing on each input image to generate a stream of "output images"; and present the stream of output images to screen 113. In certain embodiments, each of the stream of output images is presented sequentially side-by-side as two identical images—one in area 112 and one in area 114. Further, it is preferred that vision-enhancement system 100 operates so that the time delay between obtaining the input images and presenting the output images to screen 113, is as short as possible, so that a user may safely walk and interact with the environment around him/her while wearing the goggles 120.

In certain embodiments, the VE App may also provide a menu of options that allow for the modification of how vision-enhancement system 100 processes and generates an output image from an input image. Thus, for example, vision-enhancement system 100 may execute image-processing algorithms having parameters, where the parameters are changeable through the menu by, for example, setting parameter values for magnification, or the size and shape of magnification of the output image.

In embodiments the vision-enhancement system 100 provides adjustable features for matching the physiology of a user under various different settings. In an embodiment these features are pre-defined once for each user, and may be adjusted periodically during use. Thus, for example, given the spacing between screen 113 and the eyes of a user, focusing wheel 127 permits for an optimal setting of distance between the user's eyes and lens 124 and 126. In addition, lens 124 and/or 126 may include refractive error correction. Further, it is required that the viewed spacing between the images in areas 112 and 114 match the user's Inter Pupillary Distance (IPD). This may be accounted for, by example, by shifting the spacing of the output images in areas 112 and 114 to match the IPD.

In various embodiments, the user may adjust device settings by using input device 123, which may be one or more of: a touchpad, and which is electrically connected to smartphone 110, which is further programmed to modify the VE App according to such inputs; a Bluetooth game controller that communicates with the smartphone 110 via Bluetooth; voice control using the microphone of the phone; or gesture control using available devices such as the NOD gesture control ring.

In addition, there are other features of vision-enhancement system 100 that can either be set up once for a user or may be user-adjustable. These features comprise, but are not limited to, adjustments to the magnitude, shape, size, or placement of minified or magnified portions of the output image, and color enhancement functions such as contrast, blur, ambient light level or edge enhancement of the entire image or portions of the image. In some embodiments, color and color sensitivity may be set or adjusted based on a plurality of different controls. In some embodiments, color and/or color sensitivity may be adjusted by the user. In some embodiments, color and/or color sensitivity adjustments are performed by the system to optimize colors. In other embodiments, the compass and/or accelerometers within smartphone 110 may be used for enhancing orientation, location, or positioning of output images.

In certain embodiments, sound and/or vibration may be provided on smartphone 110 to generate proximity and hazard cues. In other embodiments, the microphone of smartphone 110 can be used to enter voice commands to modify the VE App. In other embodiments, image stabilization features or programming of smartphone 110 may be used to generate output images.

In an embodiment, by way of example only, goggles 120 are commercially available virtual-reality goggles, such as Samsung Gear VR (Samsung Electronics Co. Ltd., Ridgefield Park, N.J.) and smartphone 110 is a Galaxy Note 4 (Samsung Electronics Co. Ltd., Ridgefield Park, N.J.). The Samsung Gear VR includes a micro USB to provide an electrical connection to the Galaxy Note 4 and has, as input devices 123, a touch pad and buttons.

It would be apparent to persons of skill in the art that vision-enhancement system 100 may, be formed from a single device which comprises one or more cameras, a processor, display device, and lenses that provide an image to each eye of the user, instead of including a combination of smartphone and goggles. In an alternative embodiment, some of the components of the vision-enhancement system are head-mounted and the other components are in communication with the head-mounted components using wired or wireless communication. Thus, for example, the screen and, optionally the camera, may be head-mounted, while the processor communicates with the screen and camera using wired or wireless communication. In such an embodiment, an integrated processor and memory would comprise a plurality of programmatic instructions which, when executed, implement one or more of the functional modules described herein and shown in, among other places, FIG. 1F.

In embodiments, different combinations of elements may form the vision-enhancement system 100. Thus, in an embodiment, an electronic device which is not a smartphone, but which has a processor, memory, camera, and display may be mounted in goggles 120. In another embodiment, some of the electronic features described as being included in smartphone 110 may be included in goggles 120, such as the display or communications capabilities. Further, in an embodiment, the input control provided by input device 123 may be provided by a remote-control unit that is in communication with smartphone 110.

FIG. 1E illustrates an exemplary set of system components that may be incorporated in the vision enhancement system 100, in accordance with some embodiments of the present specification. In embodiments, the system components are integrated with a pair of smart goggle, or a smartphone with an attachment that enables a user to wear the smartphone like goggles. In embodiments, the system components of vision enhancement system 100 may communicate with a user interface/input device 123 that is integrated with its components, or externally connected to the system 100 through wired or wireless communication means. In some embodiments, the interface is one of: a combination of a touchpad, a voice interface, an optical interface, a motion or gesture sensor, or any other type of interface. Camera 111 and backward camera 115 are configured to receive images, which are processed by a processing unit 150. In some embodiments, processing unit 150 comprises one or more software modules, including an interface module 152 and VE App 154, which include a programmed set of instructions for processing the input signals received by the interface module 152 from the user interface, in accordance with the instructions of the VE App 154.

In some embodiments, execution of a plurality of sequences of programmatic instructions or code enables or causes the CPU of the processing unit 150 to perform various functions and processes. The processing unit 150 may be any computing device having one or more processors and one or more computer-readable storage media such as RAM, hard disk or any other optical or magnetic media. In alternate embodiments, hard-wired circuitry may be used in place of, or in combination with, software instructions for implementation of the processes of systems and methods described in this application. Thus, the systems and methods described are not limited to any specific combination of hardware and software.

The term 'module' used in this disclosure may refer to computer logic utilized to provide a desired functionality, service or operation by programming or controlling a general purpose processor. In various embodiments, a module can be implemented in hardware, firmware, software or any combination thereof. The module may be interchangeably used with unit, logic, logical block, component, or circuit, for example. The module may be the minimum unit, or part thereof, which performs one or more particular functions.

Figure 1D:
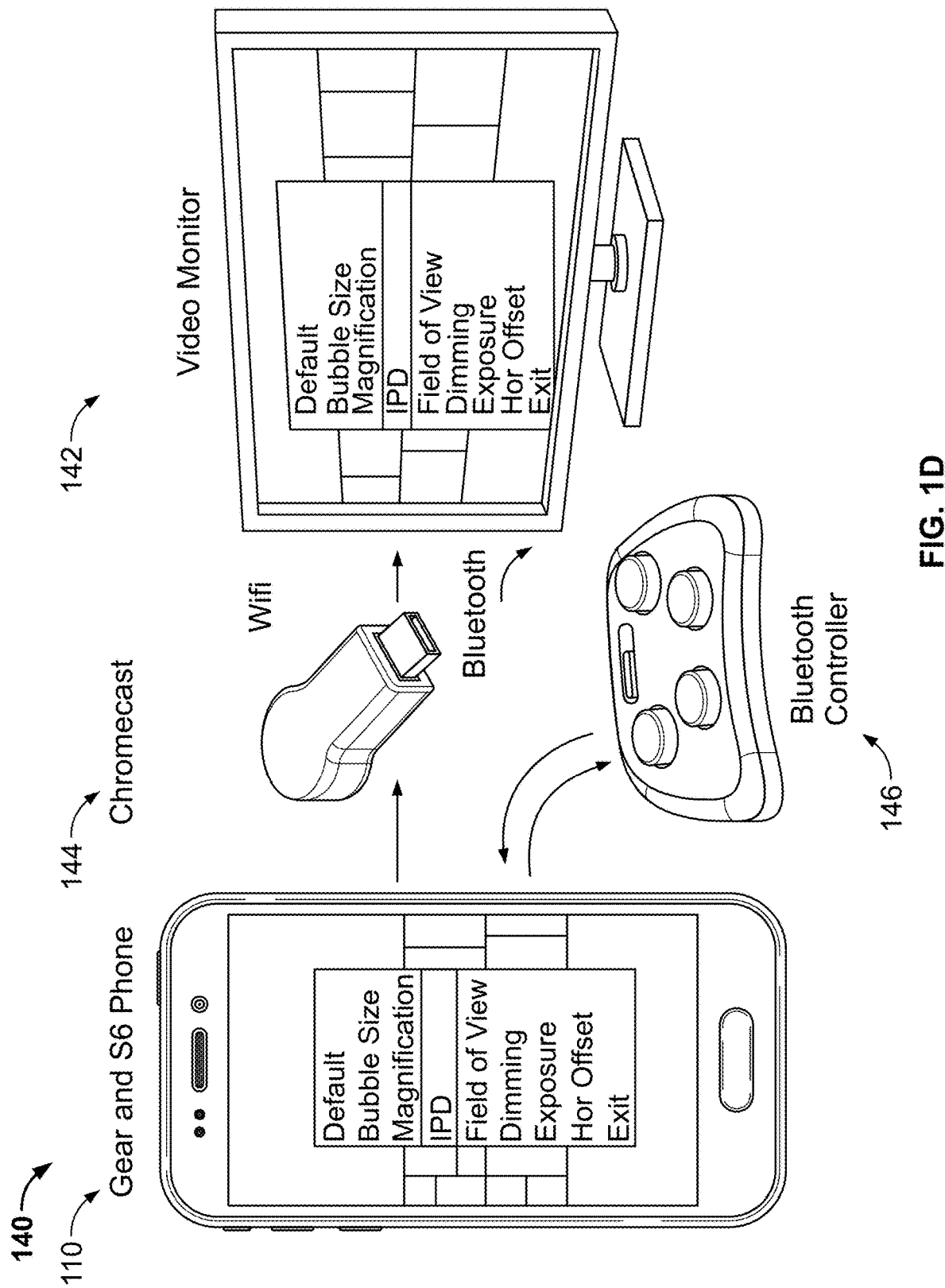
FIG. 1D illustrates an exemplary system environment including devices that may communicate with the system of FIG. 1A, in accordance with some embodiments of the present specification.

FIG. 1D illustrates, without limitation, one embodiment of a clinical setup 140 that a clinician may use to configure vision-enhancement system 100. Clinical setup 140 may allow a user or a clinician to determine and setup the VE App by setting an IPD, a field of view (FoV), background dimming, ambient light level, as well as parameters that are also user-adjustable, such as the size, shape, magnification, and location of enhanced vision features, such as the magnification bubble described subsequently. The setup may also be used by the user and/or the clinician, or any other medical or non-medical person caring for the user, to diagnose the user's vision and configure the VE App to assist the user with and/or provide therapeutic treatments to the user for, user-specific vision-related issues.

Clinical setup 140 thus allows for the adjustment of parameters within, or used by, the VE App that smartphone 110 runs to implement the vision-enhancement system 100. Clinical setup 140 includes a monitor 142, a Wi-Fi device 144 to allow screen 113 of smartphone 110 to be displayed on the monitor, and a Bluetooth controller 146 to communicate via Bluetooth with smartphone 110. In general, clinical setup 140 accepts a video output from smartphone 110 of screen/display 113, and projects what the user would see when using vision-enhancement system 100 on monitor 142.

In certain embodiments, features or aspects of the present vision-enhancement system 100 may be adjusted by a clinician using clinical setup 140. Using the vision-enhancement system 100, screen 113 of smartphone 110 is mirrored on monitor 142, using Wi-Fi device 144, for example, so that the clinician can view what the user is viewing in vision-enhancement system 100. In embodiments, Wi-Fi device 144 may refer to any other type of communication device enabling communication between the vision enhancement system 100 and one or more remote computing devices. The VE App on smartphone 110 includes a menu that allows for the selection of certain parameters that operate vision-enhancement system 100.

The clinician has access to the commands in the menu of the VE App via remote Bluetooth controller 146. In this way, the clinician can "tune" the device to the specific visual demands of the user.

In certain embodiments, Wi-Fi device 144 can be used to remotely add, augment or modify functions that allow vision-enhancements, mirror the display, monitor and control VE App configurations in a clinical environment. In certain embodiments, Bluetooth controller 146 can be used to control or modify visual enhancement functions. In certain other embodiments, the VE App may be reconfigured in a purely magnified format, making it possible for a user having reduced visual acuity to place phone calls, utilize maps, read announcements and perform all visual functions currently available to those with normal vision.

Figure 1G:
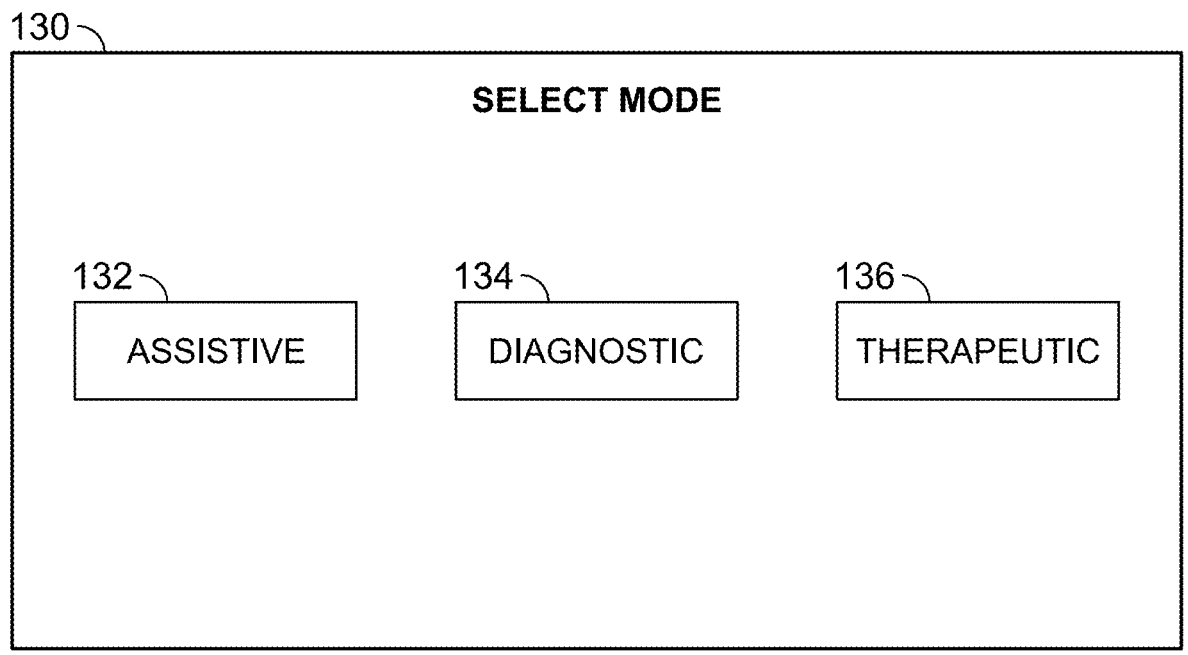
FIG. 1G illustrates an exemplary user interface enabling a user to select an operational mode, in accordance with an embodiment of the present specification.
Figure 1H:
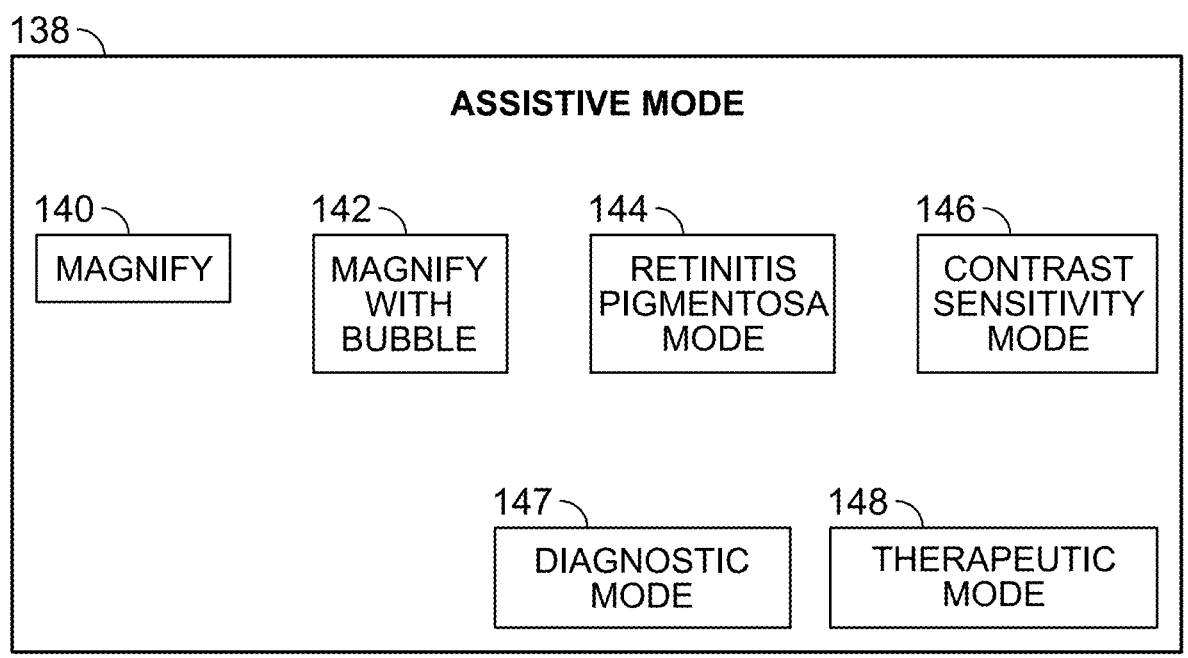
FIG. 1H illustrates an exemplary user interface presented to a user upon selecting an assistive mode of operation, in accordance with an embodiment of the present specification.

In embodiments, vision enhancement system 100 enables a user to choose a specialized processing for its operation, each specialized processing offering vision solutions for different types of user requirements. In an embodiment, an assistive mode of operation is provided. In another embodiment, a diagnostic mode of operation is provided. In yet another embodiment, a therapeutic mode of operation is provided. A user may switch between different modes by using a control provided via an interface on screen 113 of smartphone 110, on monitor 142, or via any other type of interface in communication with the vision enhancement system 100. Referring to FIG. 1F, when the aforementioned plurality of programmatic instructions are executed, a central menu 190 is generated and presented on at least one of the aforementioned display systems. A user may manipulate one or more of the aforementioned input devices to place the system into at least one of an assistive mode of operation 194, a diagnostic mode of operation 192, or a therapeutic mode of operation 196. FIG. 1G illustrates an exemplary user interface enabling a user to select an operational mode, in accordance with an embodiment of the present specification. Interface 130 displayed to a user comprises clickable/selectable buttons/options for selecting an assistive mode 132, a diagnostic mode 134 or a therapeutic mode 136 of operation. Upon clicking/selecting any one of the options 132, 134, 136 the user is presented with another user interface depending upon the selected option. Each mode of operation may further have sub-modes of operation. For example, in the assistive mode of operation 194, a user may further execute a magnification mode 194a, a magnification mode with a customizable bubble 194b, a retinitis pigmentosa mode 194c, a contrast sensitivity mode 192d, or a plurality of additional modes, extending to module 194n. FIG. 1H illustrates an exemplary user interface presented to a user upon selecting an assistive mode of operation, in accordance with an embodiment of the present specification. In an embodiment, if a user selects the assistive mode option 132 in the display interface 130, the user is presented with a display interface 138 comprising clickable/selectable buttons/options for selecting a magnification mode 140, a magnification mode with a customizable bubble 142, a retinitis pigmentosa mode 144 or a contrast sensitivity mode 146 of operation. Display 138 also comprises buttons/options 147 and 148, which upon clicking/selecting enable a user to navigate to a diagnostic mode or a therapeutic mode respectively.

Figure 1I:
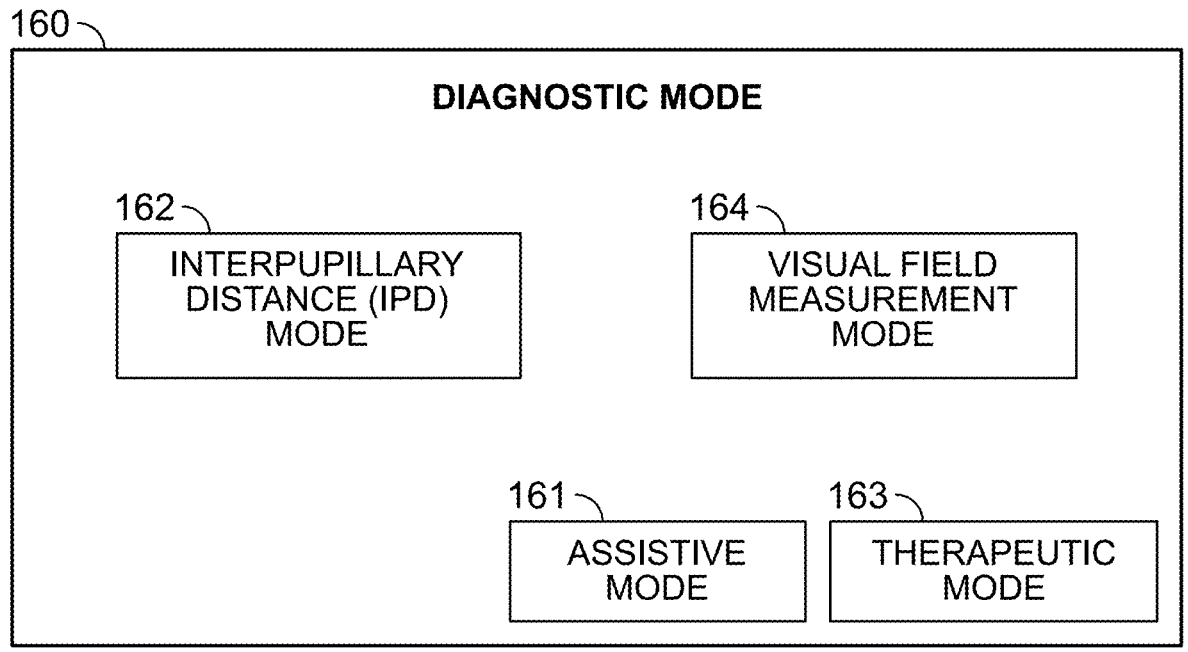
FIG. 1I illustrates an exemplary user interface presented to a user upon selecting a diagnostic mode of operation, in accordance with an embodiment of the present specification.

Referring to FIG. 1F, for example, in the diagnostic mode of operation 192, a user may further execute an interpupillary distance (IPD) mode 192a, a visual field measurement mode 192b, or a plurality of additional modes, extending from 192d to module 192n. FIG. 1I illustrates an exemplary user interface presented to a user upon selecting a diagnostic mode of operation, in accordance with an embodiment of the present specification. In an embodiment, if a user selects the diagnostic mode option 134 in the display interface 130, the user is presented with a display interface 160 comprising clickable/selectable buttons/options for selecting a interpupillary distance (IPD) mode 162, or a visual field measurement mode 164 of operation. Display 160 also comprises buttons/options 161 and 163, which upon clicking/selecting enable a user to navigate to an assistive mode or a therapeutic mode respectively.

Figure 1J:
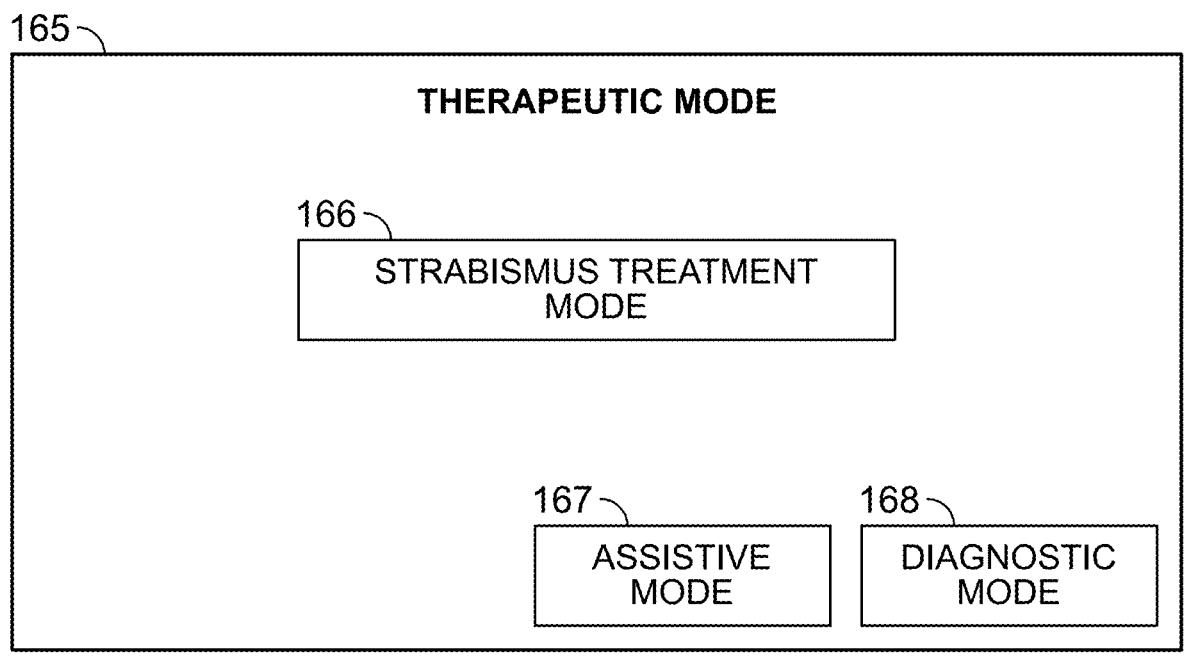
FIG. 1J illustrates an exemplary user interface presented to a user upon selecting a therapeutic mode of operation, in accordance with an embodiment of the present specification.

Referring to FIG. 1F, for example, in the therapeutic mode of operation 196, a user may further execute a strabismus treatment mode 196a or a plurality of additional modes, extending from module 196b, 196c to module 192n. FIG. 1J illustrates an exemplary user interface presented to a user upon selecting a therapeutic mode of operation, in accordance with an embodiment of the present specification. In an embodiment, if a user selects the therapeutic mode option 136 in the display interface 130, the user is presented with a display interface 165 comprising clickable/selectable buttons/options for selecting a strabismus treatment mode 166 of operation. Display 165 also comprises buttons/options 167 and 168, which upon clicking/selecting enable a user to navigate to an assistive mode or a diagnostic mode respectively.

As further discussed below, each of the aforementioned sub-modules is dedicated to particular sub-processing approaches to suit the requirement of the user.

Assistive Mode

This mode is configured to provide vision assistance to a user. The user may have a particular vision related problem, such as but not limited to Macular Degeneration (AMD), Retinitis Pigmentosa (RP), Contrast Sensitivity, or other visual issues that require assistance while seeing and navigating. Multiple sub-modes may be configured to meet the specific type of vision related problem for which the user requires assistance. The user may switch between the configured sub-modes by using a control provided via a user-interface.

Magnification Mode

This mode may assist a user with AMD. In one embodiment, the processor of vision enhancement system enables the user to obtain input video images of the scene in the front of the user, and transforms the input video images to a stream of output video images where a central portion of the scene is magnified to fit the entire screen viewed by the user. The user may modify one or more parameters of the magnified scene, such as but not limited to, the magnifying power, the contrast or the light level of the image.

Magnification with Bubble Mode

The magnification with bubble mode may also assist users with AMD. The user may switch between the magnification mode and the magnification with bubble mode, by using a control provided via a user-interface, such as switching a button. In one embodiment, the processor of the vision enhancement system 100 performs a remapping of video images viewed by the user, to magnify a central portion of the video images with a magnification bubble, to leave the peripheral portion either unmagnified or at a lower power of magnification than the bubble, and to provide a smooth transition between the magnification bubble and the peripheral portion so that the user can easily keep the magnified area within context of the viewed scene. The magnification of the scene varies smoothly across the image to prevent any discontinuities in the processed image and to assure that the remapping by itself does not introduce an additional scotoma or blind area. Thus, for example, the mapping may present an unmagnified image that contains no edges and include a magnified image at some central portion.

The vision enhancement system 100 enhances images for people with low-vision by mapping each pixel of an imaged scene to an output image viewable by the user of the system 100. The mapping is performed, in one embodiment, to provide a smoothly varying magnification across the output image such that the user of the system can easily see how the magnified region is part of the peripheral area. Thus, for example, the user of the system can see every part of the original scene without any visual discontinuities.

Figure 2:
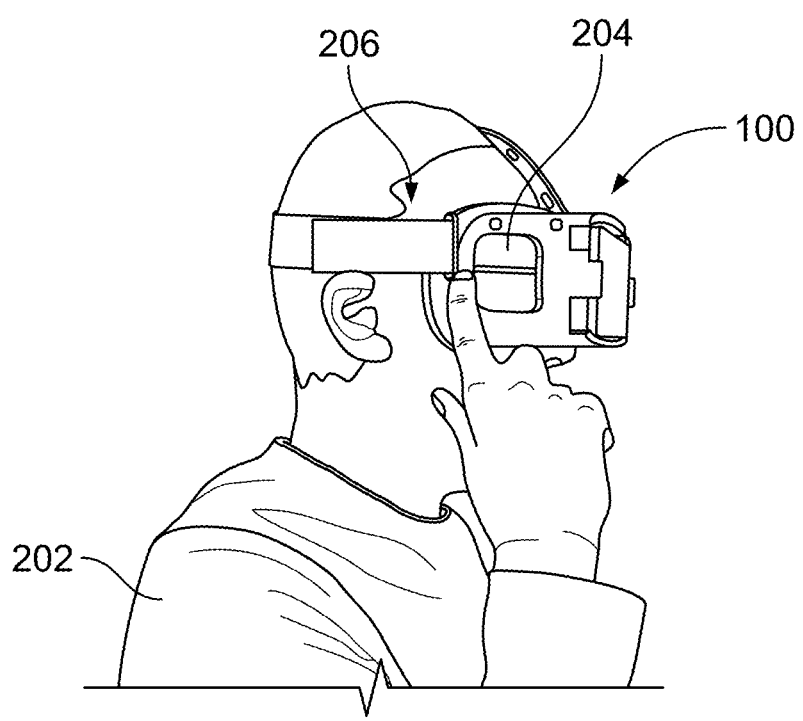
FIG. 2 illustrates an embodiment where a user interfaces with a touch pad positioned on side of a headset, to modify the enhancement in real time, in accordance with some embodiments of the present specification.

In embodiments, the user may modify the enhancement in real time. In embodiments, a touch pad, or any other type of interface, is provided with the vision enhancement system 100. FIG. 2 illustrates an embodiment where a user 202 interfaces with a touch pad 204 positioned on a side of a headset 206, for enabling the user 202 to modify the image enhancement provided by vision enhancement system 100, in real time.

Figure 3:
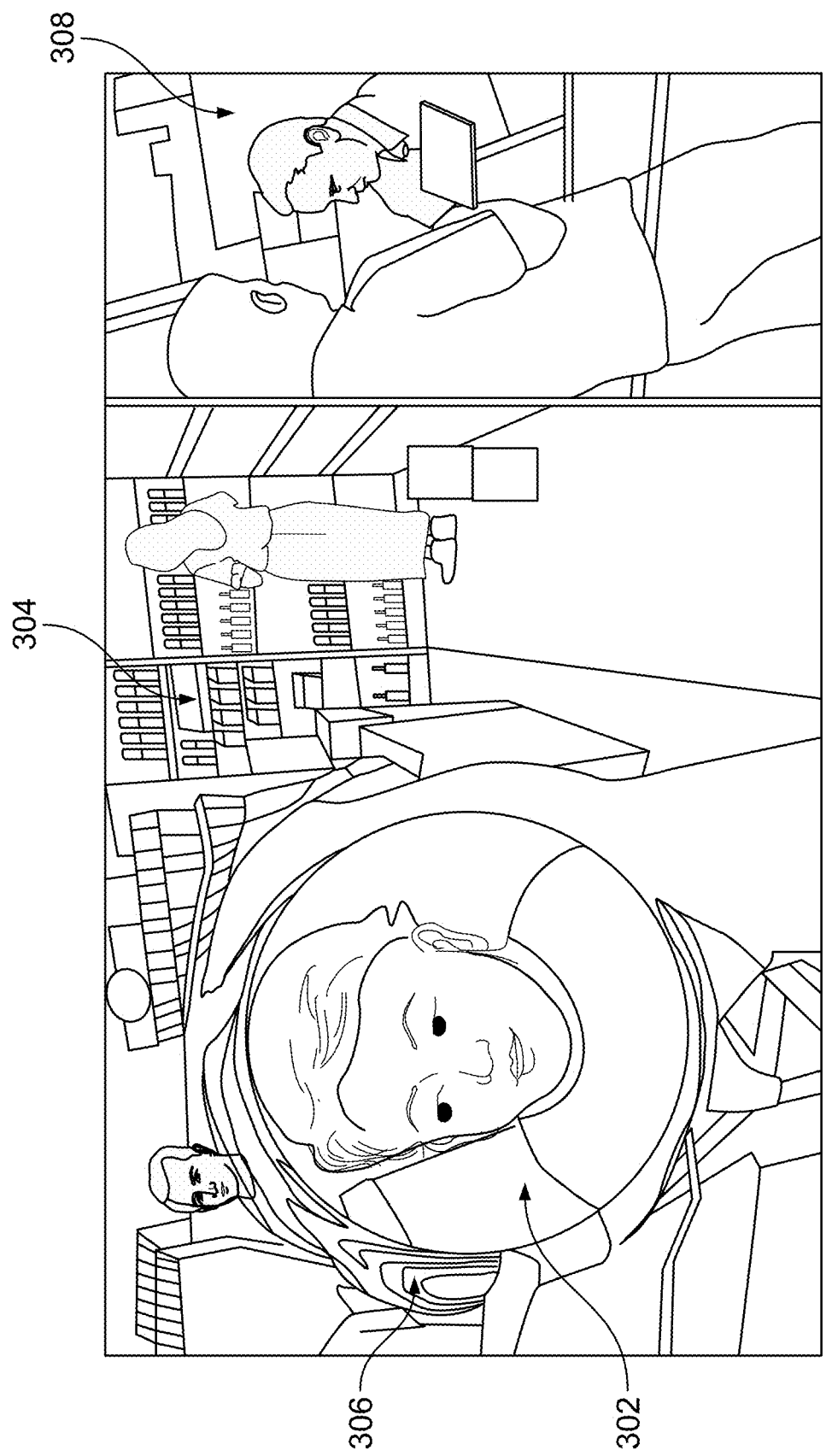
FIG. 3 illustrates a magnification bubble of a portion of a scene, in accordance with some embodiments of the present specification.

FIG. 3 illustrates a magnification bubble 302 of a portion of a scene 304. A smoothly varying transition 306 of the magnification bubble 302 surrounds the bubble 302 so that the user can see how the magnified region is part of the peripheral area 308.

Figure 4:
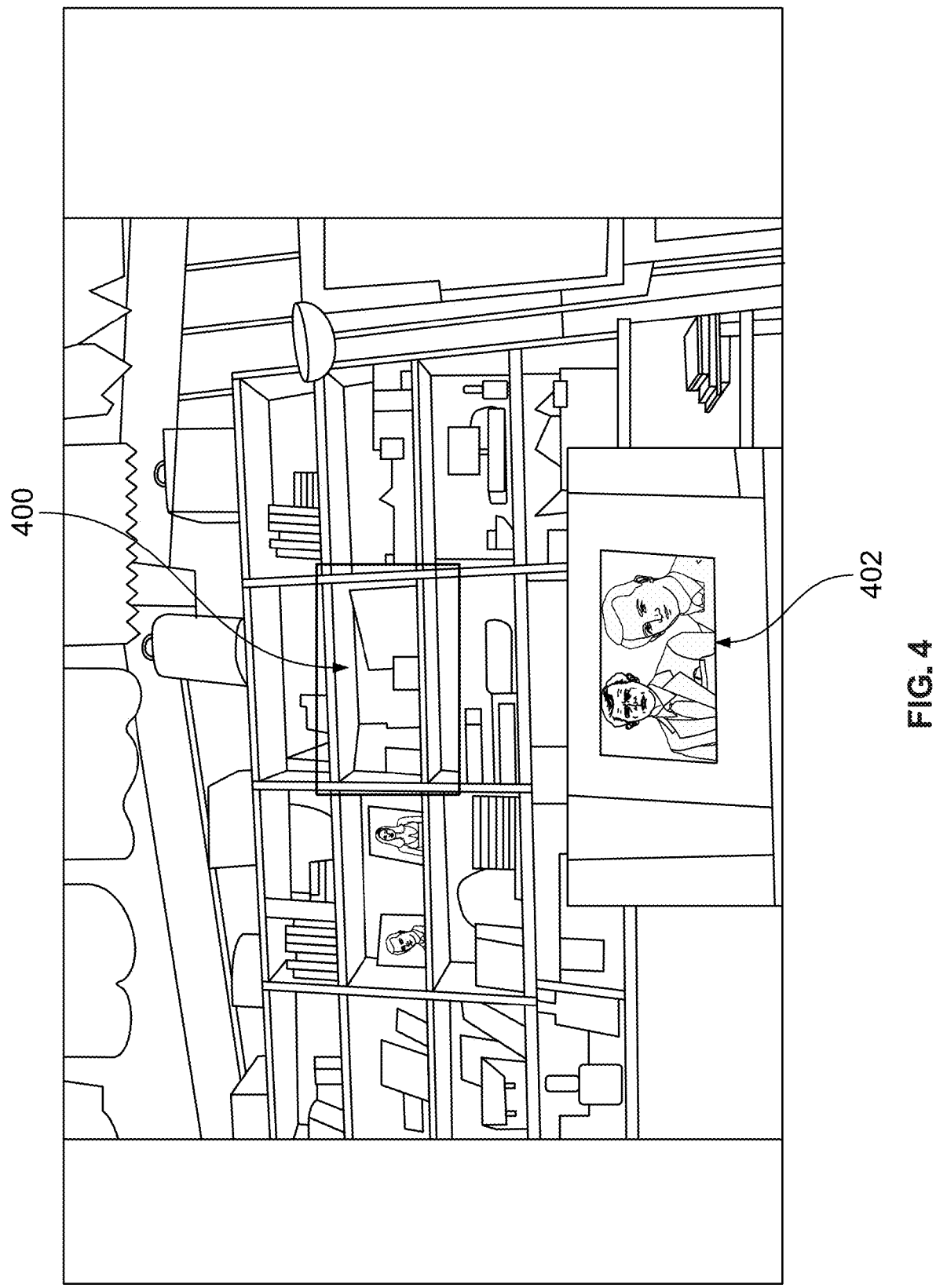
FIG. 4 illustrates a magnified portion of a scene, in accordance with some embodiments of the present specification.

FIG. 4 illustrates a magnified portion 402 of a scene 400, in accordance with some embodiments of the present specification.

U.S. Pat. Nos. 10,146,304 and 10,444,833, assigned to the Applicant, and incorporated herein in their entirety, describe systems and method that implement magnification and magnification with a bubble, in accordance with the embodiments of the present specification.

RP Mode

This mode assists users suffering from retinitis pigmentosa. As is known, the field of vision of a user is defined as that portion of space in which objects are visible to the user at the same moment during steady fixation of the user's gaze in one direction. The monocular visual field consists of central vision, which includes the inner 30 degrees of vision and central fixation, and the peripheral visual field, which extends 100 degrees laterally, 60 degrees medially, 60 degrees upward, and 75 degrees downward. In an example, a user with RP can only concurrently view 30 degrees of a 180 degrees field of view. Thus, it is difficult for the user to obtain a full concurrent understanding of what is in front of them. The user may have to view a portion of that field, and then view another portion by turning his/her head, and then mentally attempt to stitch the views together. Embodiments of the present specification overcome this difficulty in the RP mode, by processing the scene to minimize the field of view, obtain a full normal visual field view (as described above), and then compact said view into a predetermined smaller field of view, while maintaining the scale and perspective of said view.

In an embodiment, the vision enhancement device is configured to process a scene by minimizing the scene. The processor is operated to present an image of adjustable size and present a scene within a smaller field of view than what would be viewed with normal vision. The visual field is viewed in a manner that is similar to looking through a soda straw In one embodiment, a normal visual field that would encompass an inner 30 degrees of vision and central fixation and a peripheral visual field, which extends 100 degrees laterally, 60 degrees medially, 60 degrees upward, and 75 degrees downward is minimized such that the entirety of that visual field, or all images in the central and peripheral visual field, are scaled down to fit within the minimized visual field of the patient, which may be in a range of 90% to 5% of any dimension of the normal visual field.

For example, a normal visual field extending 100 degrees laterally, 60 degrees medially, 60 degrees upward, and 75 degrees downward is minimized such that the entirety of that visual field, or all images in the central and peripheral visual field, are scaled down to fit within a visual field extending 50 degrees laterally, 30 degrees medially, 30 degrees upward, and 37.5 degrees downward, equating to a 50% scaling down of the entire normal visual field. In one embodiment, each dimension of the visual field (lateral, median, up and down), which may not be equal in all directions, is subjected to the same degree of scaling. In another embodiment, each dimension of the visual field (lateral, median, up and down), which may not be equal in all directions, is subjected to a different degree of scaling.

In another example, a user with RP can only concurrently view 30 degrees of a wider field of view. Thus, it is difficult for the user to obtain a full concurrent understanding of what is in front of them. The user may have to view a portion of that field, and then view another portion by turning his/her head, and then mentally attempt to stitch the views together. Embodiments of the present specification overcome this difficulty in the RP mode, by processing the scene to minimize the field of view, obtain a full normal visual field view (as described above), and then compact said view into a predetermined smaller field of view, while maintaining the scale and perspective of said view.

In order to achieve output video images that occupy a smaller field of view than corresponding input video images, in an embodiment, the processor of vision enhancement system 100 is configured to provide a zoomed-out version of the input images, which may be understood as being similar to looking through a "wrong" end of a telescope. The zoomed-out images are referred to herein as being "minified" which is the opposite of being magnified. This minified view gives the user a contextual view of a scene being viewed. The program is also operable in response to a command by the patient after viewing the contextual scene to magnify the scene so as to focus in on a particular feature of the scene (another person's face, a label on a package, title of a book, etc.). In embodiments, a screen is disposed to display the output video images for viewing by the user. A user-interface enables the user to generate an input to the processor for adjusting the size of the output video images. In embodiments, the user may adjust the size of the output video images of the scene to occupy less than 35 degrees of the field of view of the user.

Referring to FIGS. 1A 1B, in one embodiment, the VE App is made accessible via smartphone 110 which performs image processing on each image of the stream of video images and then presents each processed area of the images, simultaneously, to areas 112 and 114. VE App starts the method, which runs continuously until stopped by the user. The VE App captures images from a scene. Images from a stream of images are read from camera into a memory. Depending on the architecture of the smartphone 110 and the capabilities and performance of the camera and the processing CPU, in embodiments, either the entire image is read into the smartphone 110 memory and then all pixels in the image are processed simultaneously, or a collection of pixels (essentially a slice of the image) are read into the smartphone 110 memory and processed it while another slice of the image is being read. The VE App then determines the size of the image output area. The size of the image output area may be preset in the VE App or may be controllable through input device 123. Subsequently, the VE App minifies the captured image to fit within output area, and optionally blackens the area between output area and the edge of areas 112/114. Finally, the VE App accepts input from input device 123 to magnify the minified image.

Figure 6A:
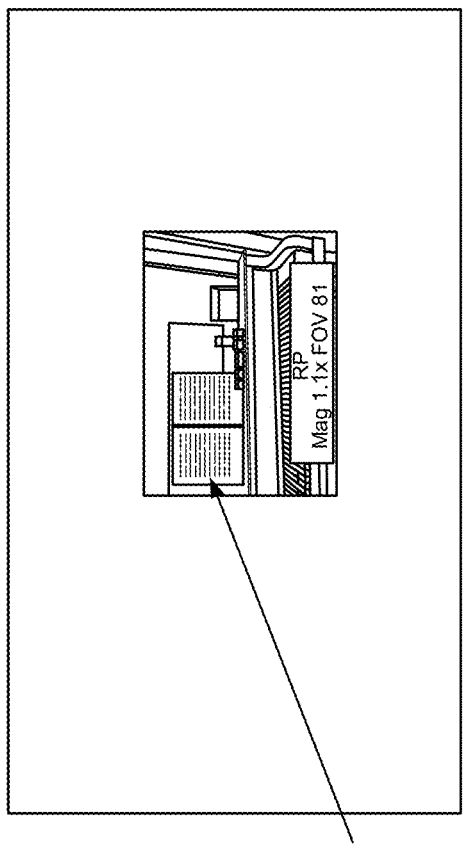
FIG. 6A illustrates a scene that is minified with the same magnification of 1.1 times, but a FoV of 35 degrees, in accordance with some embodiments of the present specification.
Figure 6B:
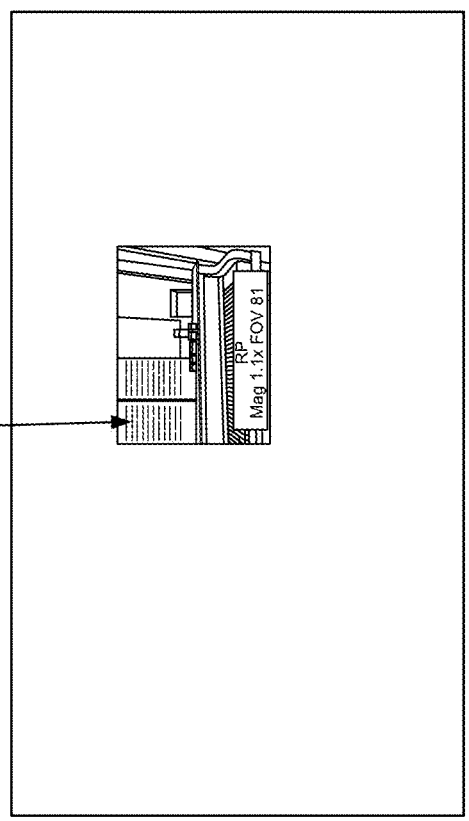
FIG. 6B illustrates a scene that can be viewed by the same user of FIG. 5 with a magnification of 2.2 times, such that the minified image appears to zoom-in to a central portion of the scene, in accordance with some embodiments of the present specification.
Figure 5:
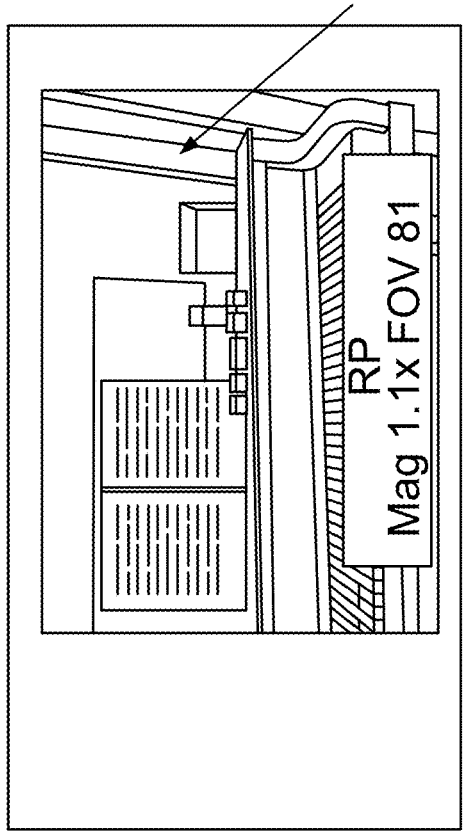
FIG. 5 illustrates a scene is viewed by the user with 1.1 times magnification of the video and a Field of View (FoV) of 81 degrees, in accordance with some embodiments of the present specification.

In embodiments, the user is provided control over the degree of minification, similar to the control provided over magnification and the magnification bubble. FIGS. 5, 6A, and 6B, illustrate exemplary views available to a user by exercising different controls while viewing a scene 500. As shown in FIG. 5, scene 500 is viewed by the user with 1.1 times magnification of the video and a Field of View (FoV) of 81 degrees. In FIG. 6A, scene 500 is minified with the same magnification of 1.1 times, but a FoV of 35 degrees is selected. In FIG. 6B, scene 500 can be viewed by the same user with a magnification of 2.2 times, such that the minified image appears to zoom-in to a central portion of the scene 500. The user is enabled to adjust the size of the scene 500 to a comfortable level. In embodiments, the comfort level of the user may vary for different types of scenes. A portrait or a face of a person or an object in close vicinity of the user may prompt for a different adjustment of the level of minification as opposed to a view of a landscape.

Contrast Sensitivity

A contrast sensitivity test or diagnostic measures a patient's ability to read between smoothly varying increment of light versus dark, otherwise also known as contrast. This test is important for determining visual function in situations of low light or when the contrast between different object and/or their environment is reduced. Most patients that have macular degeneration lose the ability to envision the low frequency end of the light spectrum. Some patients lose sight of other frequencies in the spectrum as well. Embodiments of the vision enhancement system 100 of the present specification use methods such as, but not limited to, Gabor and Landolt C method to measure contrast sensitivity, and then extrapolate the log of contrast sensitivity vs log of frequency function, for obtaining acuity of vision. The Gabor and Landolt C methods are well-known standards used for visual acuity testing and for evaluating contrast sensitivity (CS).

In accordance with some embodiments, vision enhancement system 100 is configured to determine the spatial range of frequency over which a user is experiencing a loss of vision or contrast sensitivity. The spatial range of frequencies over which the user experiences loss is determined by measuring the contrast sensitivity function of the user at a number of different spatial frequencies. The system 100 then processes the input image, so as to compensate for the determined loss of frequencies in the light spectrum that are specific to the user.

Figure 7A:
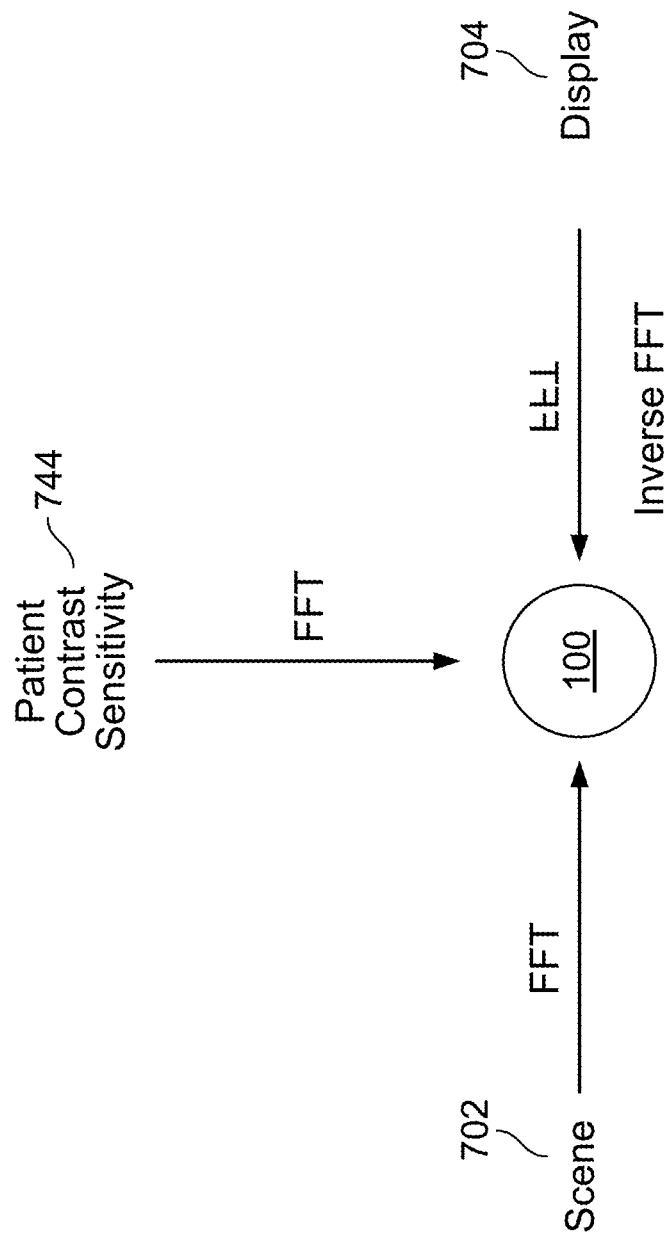
FIG. 7A illustrates an exemplary process of processing an input image from a scene, by the vision enhancement system, so as to obtain a contrast sensitivity-corrected output image, in accordance with some embodiments of the present specification.
Figure 7B:
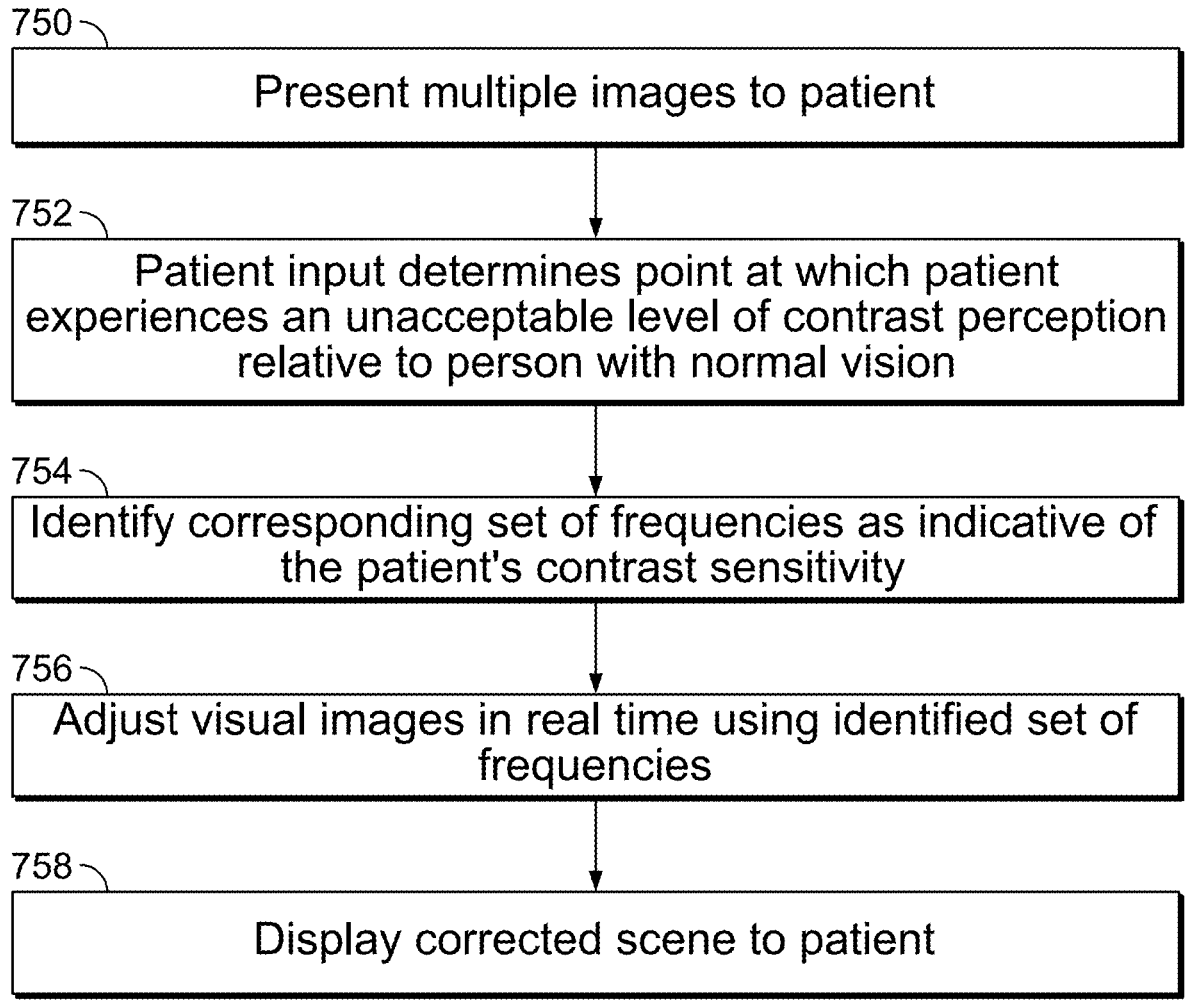
FIG. 7B illustrates an exemplary flow chart describing the process of FIG. 7A.

FIG. 7A illustrates an exemplary process of processing an input image from a scene 702, by the vision enhancement system 100, for obtaining a contrast-corrected output image 704, in accordance with some embodiments of the present specification. FIG. 7B illustrates an exemplary flow chart describing the process illustrated in FIG. 7A. FIG. 8A illustrates a visual image presented to a user during the process illustrated in FIG. 7A. Referring simultaneously to FIGS. 7A, 7B and 8A, in embodiments, at step 750, a patient is first assessed for contrast sensitivity by presenting a plurality of visual image such as image 802, and at step 752, determining at what point a user experiences an unacceptable level of contrast perception, relative to how a person with normal vision would process the visual images 802. It should be appreciated that the visual image 802 is generated by the software platform, as described above, and presented in one or more of the above-mentioned displays of the vision enhancement system of the present specification. It should further be appreciated that the system generates one or more prompts, and receives one or more user inputs, using the above-described hardware.

Upon presenting the visual image 802, if the patient finds a specific row/region/point 801 to be too light to see effectively, the patient would input into the system a response identifying said row/region/point 801 to be too light to effectively see. The system compares the contrast of the identified row/region/point 801 to what a person of normal vision would identify and, if there is a difference, determines a corresponding set of frequencies that are associated with the discrepancy between the contrast of the identified row/region/point 801 and what a person of normal vision would identify as sufficiently visible. At step 754, the system identifies and stores the corresponding set of frequencies as indicative of the patient's contrast sensitivity 744.

Figure 8B:
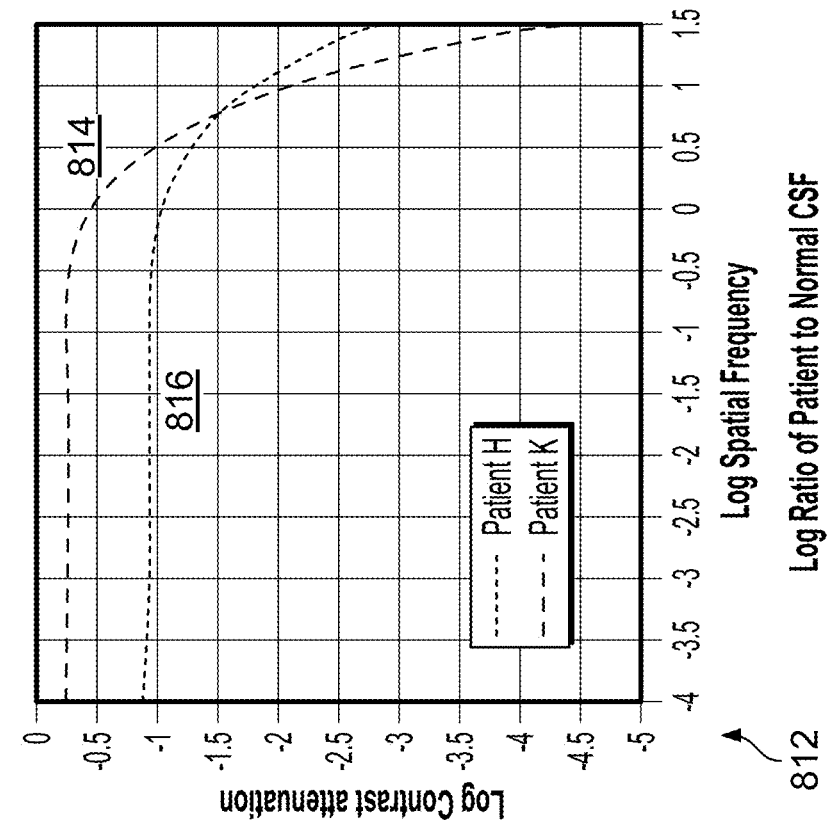
FIG. 8B illustrates an exemplary graph showing Contrast Sensitivity (CS) curve for a user with normal CS, and curves for users with diseased CS.
Figure 8B:
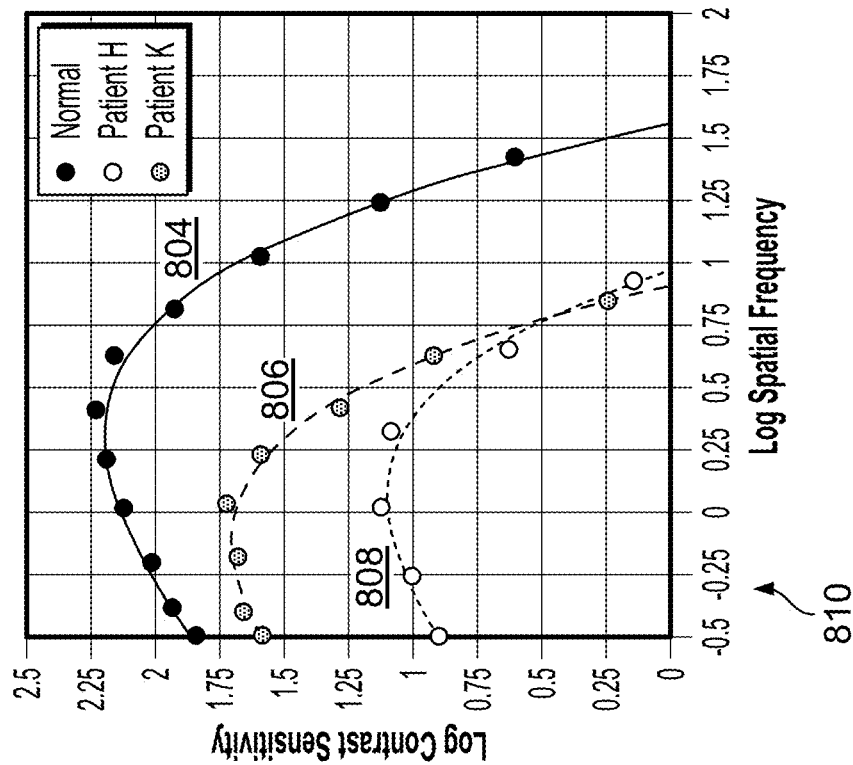

While the image 802, which represents a contrast sensitivity chart, may be used to measure contrast sensitivity of the user, and therefore determine the spatial frequencies where the user experiences contrast sensitivity issues, it should be appreciated that contrast images other than that shown in FIG. 8A may be used, provided the images display a varying degree of contrast. FIG. 8B illustrates an exemplary graph 810 showing contrast sensitivity (CS) curve 804 for a user with normal CS, and curves 806 and 808 indicate CS for two different visually compromised users. The CS curves are formed by graphing a log of contrast sensitivity against a log of the associated spatial frequencies. As shown in the graph 810, curves 806 and 808 indicate CS that are lower than that of the normal CS curve 804. A patient corresponding to the curve 808 has a larger loss of contrast sensitivity relative to normal curve 804, than does patient corresponding to the curve 806. However, patients corresponding to the curves 806 and 808 have nearly identical visual acuities, identified from their cutoff frequencies. The cutoff frequency is the spatial frequency at which the curves 806 and 808 intersect the horizontal axis at 0 log contrast sensitivity.

A graph 812 shows a log ratio of compromised CS to normal CS for the two patients corresponding to the curves 806 and 808. In the graph 812, a line 814 corresponds to the curve 806, and a line 816 corresponds to the curve 808. Lines 814 and 816 are "error" curves that can be used to increase contrast at the compromised frequencies presented in the display. The contrast sensitivity function (CSF) is similar to a modulation transfer function. When a person whose vision is not impaired looks at an image, a Fourier transform of the image is multiplied by a predefined normal CSF. In order to simulate how an image will appear to a patient, the Fourier transform of the image is multiplied by a ratio of the patient's CSF to the normal CSF. This ratio as a function of spatial frequency is the filter function, which is shown on the log scale in the graph 812 for patients corresponding to the curves 806 and 808.

Figure 8C:
FIG. 8C illustrates an image as viewed by a person with normal vision as viewed by patients with compromised visions, in accordance with some embodiments of the present specification.
Figure 8C:
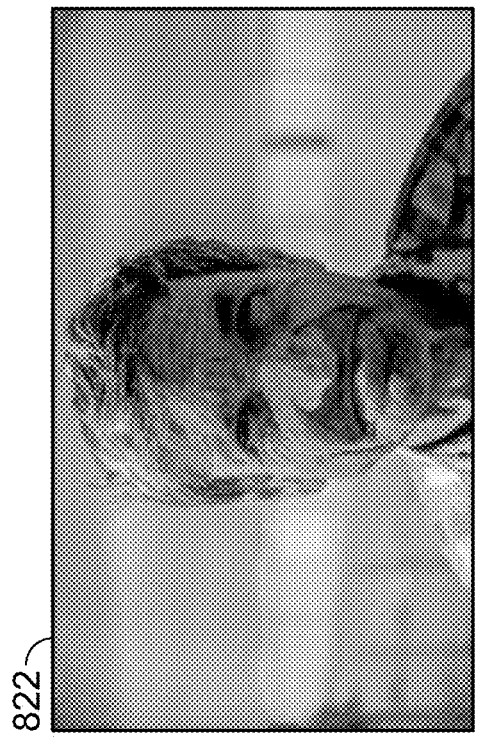
Figure 8C:
Figure 8D:
FIG. 8D illustrates an image as viewed by a person with normal vision as viewed by patients with compromised visions, when magnified two times, in accordance with some embodiments of the present specification.
Figure 8D:
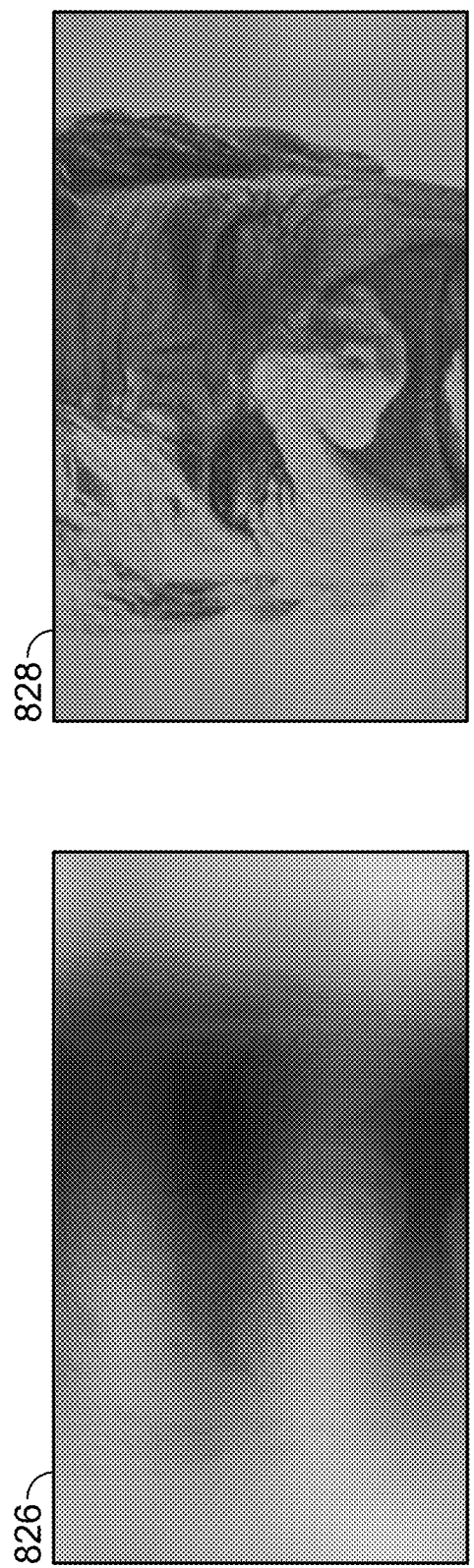
Figure 8E:
FIG. 8E illustrates an image as viewed by a person with normal vision as viewed by patients with compromised visions, when magnified four times, in accordance with some embodiments of the present specification.
Figure 8E:
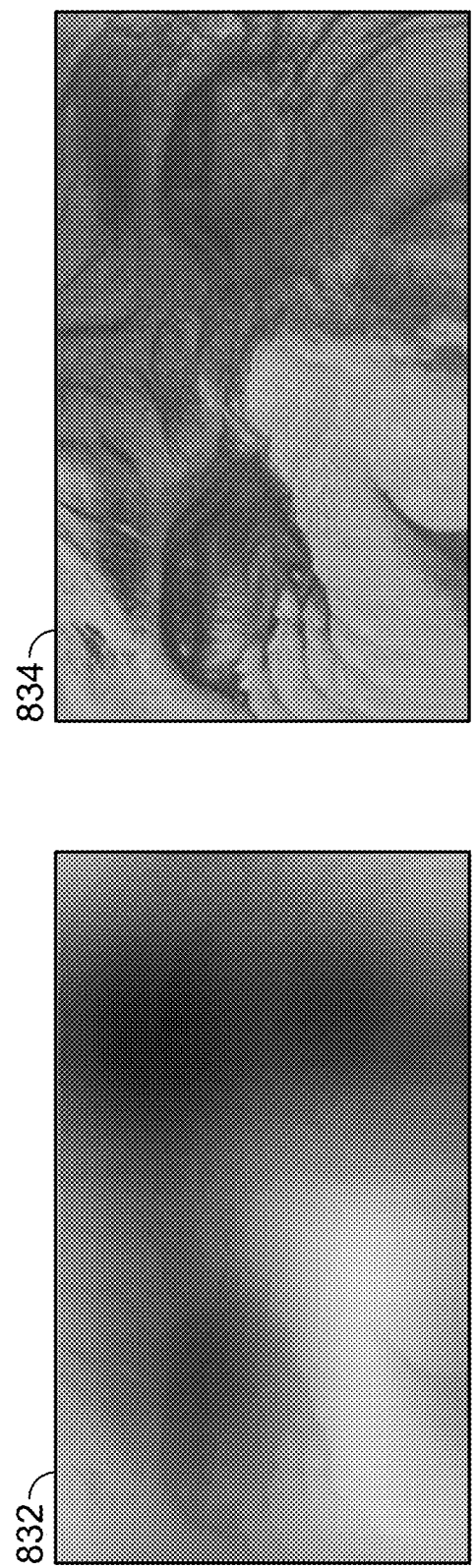

Referring to FIG. 8C, an image 818 as viewed by a person with a normal vision is viewed as image 820 by the patient corresponding to curve 808/816, and as image 822 by the patient corresponding to curve 806/814. The images 820 and 822 are obtained by multiplying the Fourier transform of image 818 by the patients' respective filter functions 816 and 814. FIG. 8D illustrates the image 818 magnified by two times into an image 824 as viewed by a person with normal vision. Image 824 is viewed as image 826 by the patient corresponding to curve 808/816, and as image 828 by the patient corresponding to curve 806/814. Magnifying the original image 818 by two times is equivalent to shifting the Fourier spectrum to lower frequencies by a factor of 2. FIG. 8E illustrates the image 818 magnified by four times into an image 830 as viewed by a person with normal vision. Image 830 is viewed as image 832 by the patient of curve 808/816, and as image 834 by the patient corresponding to curve 806/814. It may be observed from FIGS. 8D and 8E, that magnification is beneficial for the patient corresponding to curve 806/814, but is of limited value for the patient corresponding to curve 808/816.

Patients may lose contrast sensitivity (CS) with age and with visual dysfunction. In an embodiment, the CS of a patient is at least partially restored by measuring the patient's CS loss. In an embodiment, the fast Fourier transform (FFT) of a scene corresponding to a set of coefficients for the scene without any CS loss as a function of frequency for the scene is obtained. The obtained coefficients are then modified using coefficients derived from the patient's error measurements while observing the scene. The inverse FFT of the modified coefficients are used to generate a CS corrected scene, corrected for the patient.

Referring to FIGS. 7A and 7B, at step 756, during use of the vision enhancement device described herein, as a user views his/her surroundings, the contrast sensitivity module 192d receives the visual images being generated in real-time and adjusts them using the stored set of frequencies which are indicative of the patient's contrast sensitivity 744. Referring to FIG. 7A, a Fast Fourier Transform (FFT) of the scene 702 is obtained to derive an assessment of the frequencies associated with the visual images acquired in real-time. A set of coefficients as a function of frequency are obtained from the FFT of a scene viewed by the user. The stored set of frequencies indicative of the patient's contrast sensitivity 744 is then applied to the data obtained from the scene in order to subject different spatial frequencies in the FFT to an adjustment, such as a gain. Once the adjustment is made, an inverse FFT is applied to yield a data set which can be processed into adjusted real-time images. In those adjusted real-time images, energy at the spatial frequencies where the user has decreased sensitivity would be increased, resulting in a contrast sensitivity-corrected scene 704. In an embodiment, the ratio of the spatial frequency-rescaled normal CSF to a patient's CSF is used with rescaling of the normal CSF designed to equate cut-off frequencies (visual acuities) in order to obtain CS compensation by using FFT.

Figure 8F:
FIG. 8F illustrates images seen by patients after adjusting for contrast sensitivity loss, in accordance with some embodiments of the present specification.
Figure 8F:
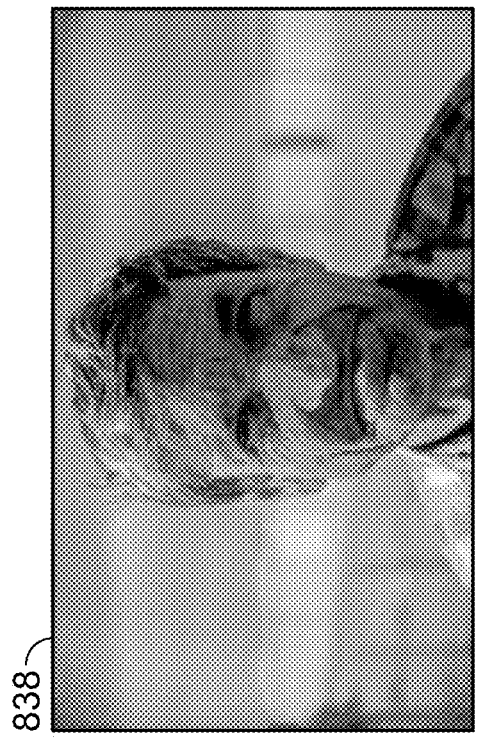
Figure 8F:

Referring to FIG. 8F, contrast sensitivity loss is compensated by taking the ratio of the normal contrast sensitivity to the patient's contrast sensitivity and multiplying the Fourier transform of the original image 818 by that ratio, as a function of spatial frequency. This is the contrast enhancement function, which is the inverse of the filter function of the graph 812 shown in FIG. 8B. However, the compensation may not be perfect as it is not possible to exceed 100% contrast. Therefore, in embodiments of the present specification the amplitudes of the signals comprising the image(s) are clipped at a predefined maximum and/or minimum if the product of the Fourier transform and the contrast enhancement function exceeds 100% contrast. Additionally, the mean luminance of the image 818 must remain fixed in order to not saturate the display 110 with the inverse Fourier transform of the enhanced image. In embodiments, the ceiling and floor corrections, corresponding to the amplitude and luminance, are built into the compensation algorithm of system 100, which generate images 836 for the patient corresponding to curve 816 and 838 for the patient corresponding to curve 814. Thus images 836 and 838 are the compensation images for the patients corresponding to curves 816 and 814, respectively. The compensation images 836 and 838 correct for the patient's loss of contrast sensitivity at each spatial frequency using the patient's contrast enhancement function for no magnification.

Figure 8G:
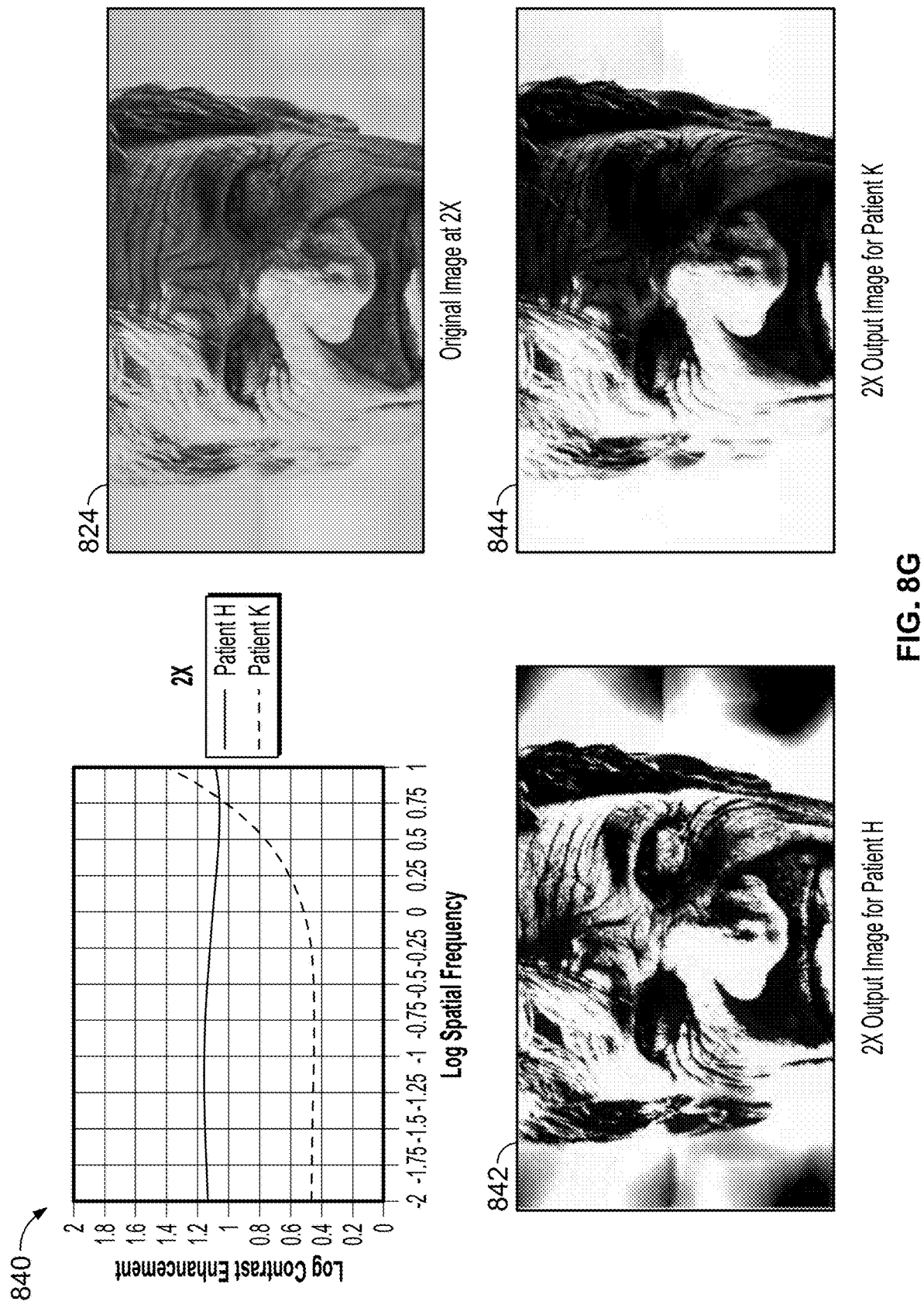
FIG. 8G illustrates images seen by patients after adjusting for contrast sensitivity loss, when magnified two times, in accordance with some embodiments of the present specification.
Figure 8H:
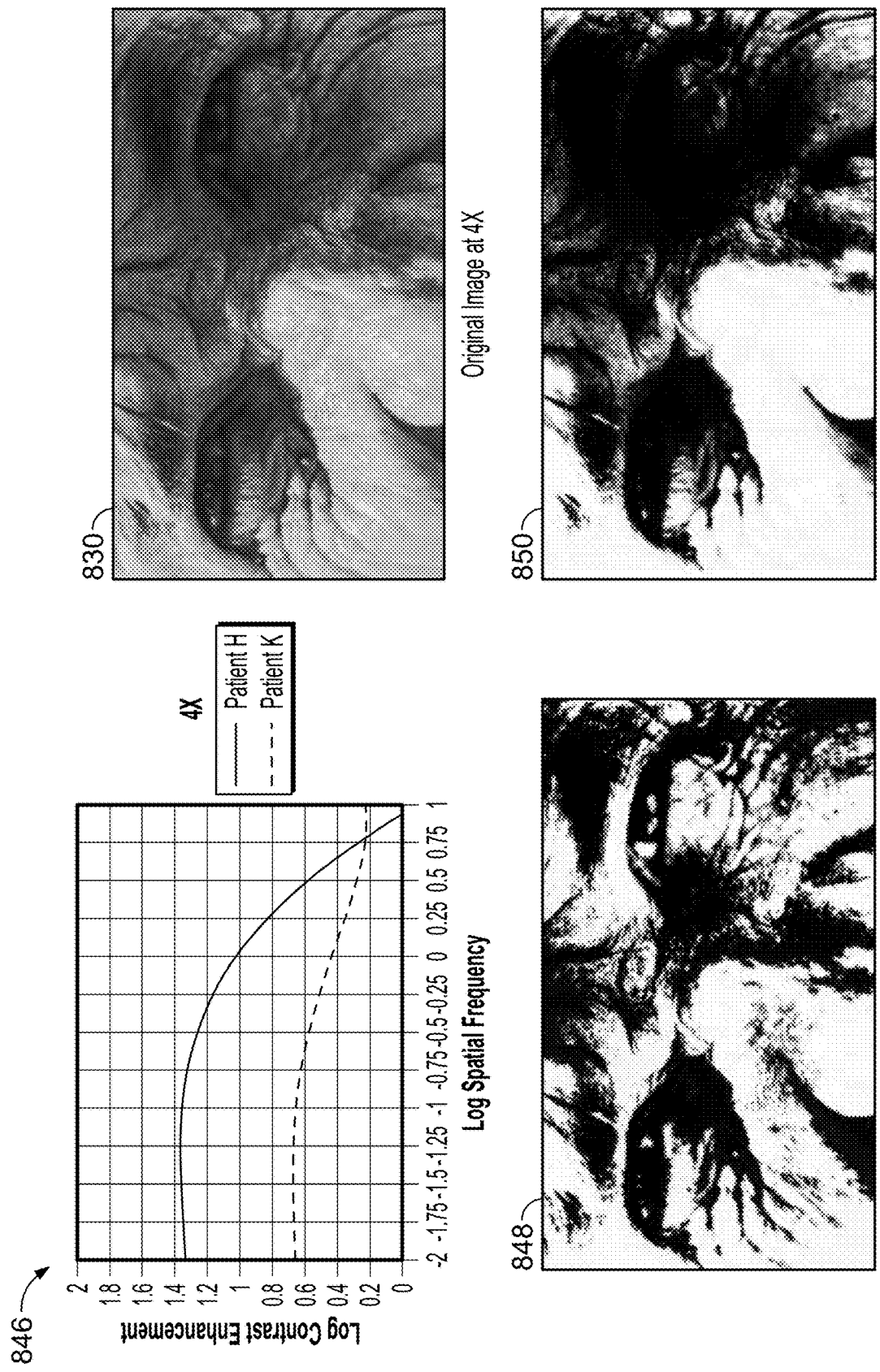
FIG. 8H illustrates images seen by patients after adjusting for contrast sensitivity loss, when magnified four times, in accordance with some embodiments of the present specification.

FIG. 8G illustrates contrast enhancement functions for the two patients, for two times magnification of the original image, as shown in image 824 of FIG. 8D. A graph 840 shown in FIG. 8G illustrates the "error" curves obtained with two times magnification, where the curves can be used to increase contrast at the compromised frequencies presented in the display. Magnification is used to shift the image spectrum of image 824 to lower frequencies and then enhance contrast to match the detail seen by the normally sighted person with one-time magnification (image 818). Thus the contrast enhancement function is specific to the amount of magnification used to compensate for loss of resolution, as shown in graph 840. The figure also illustrates examples of a compensated image 842 for the patient corresponding to curve 816 and image 844 for the patient corresponding to curve 814. Similarly, FIG. 8H illustrates a graph 846 for "error" curves obtained with four times magnification, and corresponding compensated images 848 and 850 obtained for the patients corresponding to curves 816 and 814 respectively.

Figure 8I:
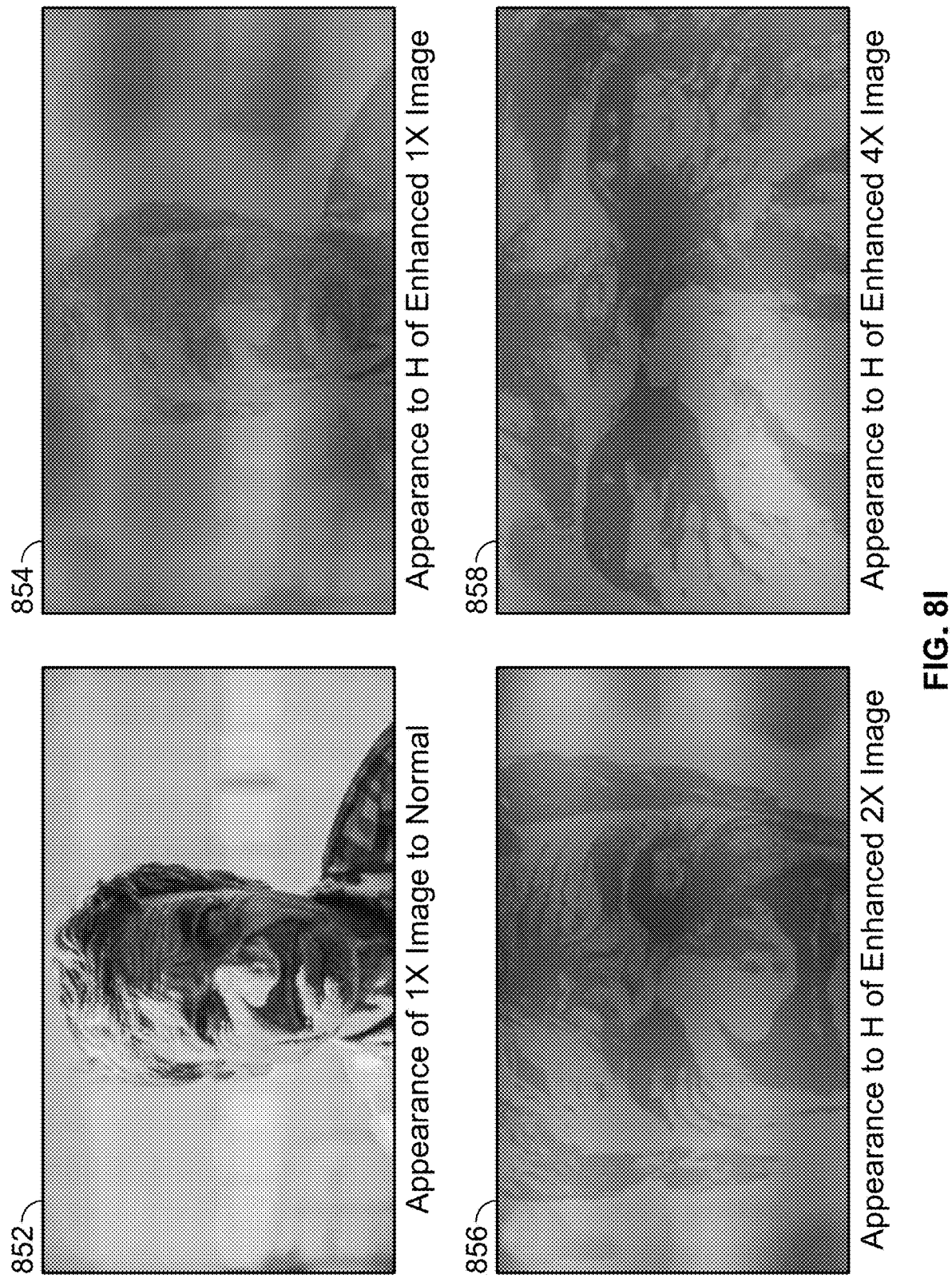
FIG. 8I illustrates comparison of differently adjusted images shown to a patient with a first type of compromised vision, in accordance with some embodiments of the present specification.
Figure 8J:
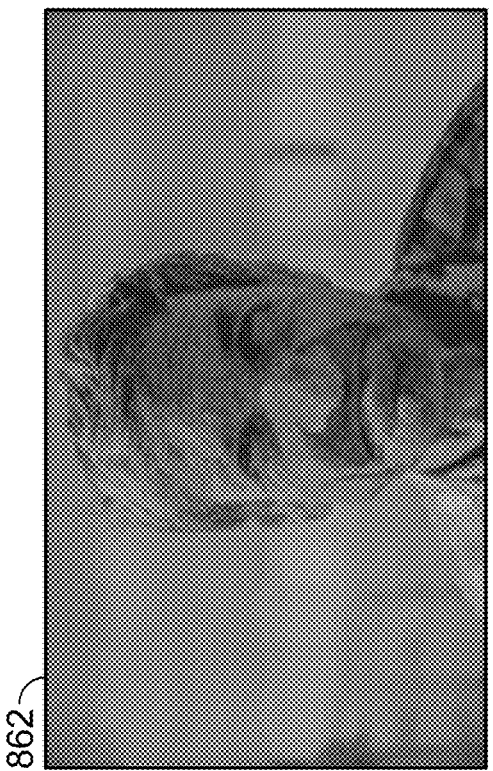
FIG. 8J illustrates comparison of differently adjusted images shown to a patient with a second type of compromised vision, in accordance with some embodiments of the present specification.
Figure 8J:
Figure 8J:
Figure 8J:
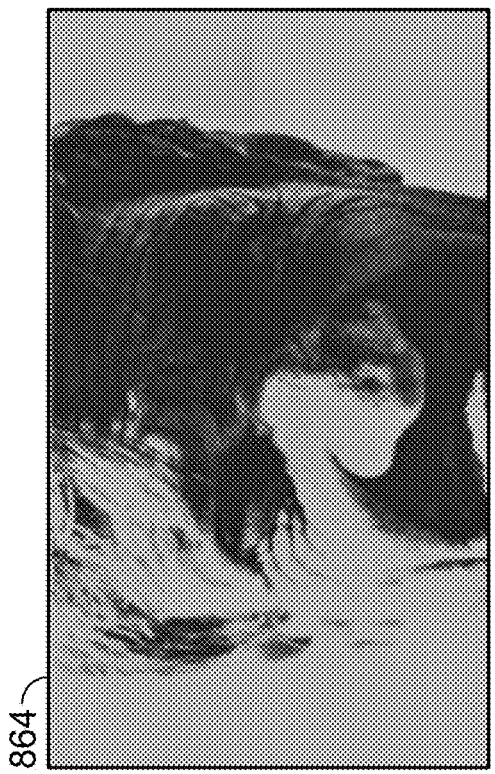

Therefore, both magnification and contrast enhancement are used to compensate for visual impairments (loss of visual acuity and loss of contrast sensitivity). Referring to FIG. 8I, an objective of the embodiments of the present specification is to make the same detail seen by a normally sighted observer in an image 852, visible to a patient H corresponding to curve 816, through a combination of magnification and customized contrast enhancements dictated by the patient's contrast sensitivity function and by the level of magnification. Thus, images 854, 856, and 858, illustrate the adjusted images shown to patient H with one time magnification, two times magnification, and four times magnification, respectively. Similarly, FIG. 8J illustrates detail seen by a normally sighted observer in an image 860, visible to a patient K corresponding to curve 814, through a combination of magnification and customized contrast enhancements dictated by the patient's contrast sensitivity function and by the level of magnification. Images 862, 864, and 866, are the adjusted images shown to a patient K with one time magnification, two times magnification, and four times magnification, respectively. Referring simultaneously to FIGS. 8I and 8J, patient K (FIG. 8J) has the same visual acuity, but better contrast sensitivity than does patient H (FIG. 8I). Therefore, less contrast enhancement is needed to obtain optimal compensation for patient K than for patient H.

Referring again to FIGS. 1A, 7A and 7B, at step 758, the corrected scene 704 is displayed to the user over a display such as display 110. In embodiments, the patient visual acuity and contrast sensitivity data is acquired at the time of an initial setup of the system 100 for its user while the adjustments are provided throughout use and in real-time as the patient views his or her surroundings using the vision enhancement system 100. It should be appreciated that this contrast sensitivity compensation approach is different from a user simply manually adjusting "contrast" on a screen. Here, the user is formally evaluated to determine what frequencies the user may not be able to see well, which the user himself or herself often fails to appreciate, and then uses that formally obtained, predetermined set of frequencies to automatically adjust images.

Diagnostic Mode

The diagnostic mode may include sub-modes to diagnose vision-related issues, by users such as patients and clinicians. Exemplary sub-modes may comprise, but are not limited to diagnosing contrast sensitivity, as described above, assessing interpupillary distance (IPD), and assessing visual field measurement.

IPD Mode

This mode is used to assist the user with alignment of eye separation with separation of two images on a display. Vision-enhancement system 100 has adjustable features that allow it to match the physiology of the user for use in different settings. These features are generally set once for each user, possibly with the need for periodic adjustment. Referring to FIGS. 1B, 1C, for example, given the spacing between screen 113 and the eyes of user U, focusing wheel 127 permits for an optimal setting of the distance to lens 124 and 126. In addition, lens 124 and/or 126 may include refractive error correction. Further, it is important that the viewed spacing between the images in areas 112 and 114 match the user's IPD. This may be accounted for, by example, by shifting the spacing of the output images in areas 112 and 114 to match the IPD. Clinical setup 140 may allow a user or a clinician to determine and setup the VE App by setting an IPD for the user.

There is a broad range over which a user may move the IPD and initially feel fine. However, eye strain may occur before the user sees a double image. Thus, it is important to have the IPD perfectly aligned from the outset of viewing. Vision-enhancement system 100 enables the user to achieve perfect alignment at the outset by allowing the user or a clinician to adjust the IPD of the system to match the user's IPD.

Figure 9A:
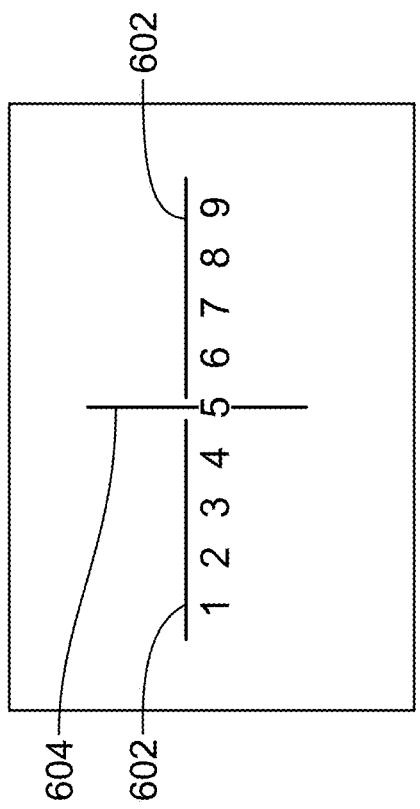
FIG. 9A illustrates a horizontal line that is presented to one eye of a user, and a vertical line that is presented to the other eye, in accordance with some embodiments of the present specification.
Figure 9C:
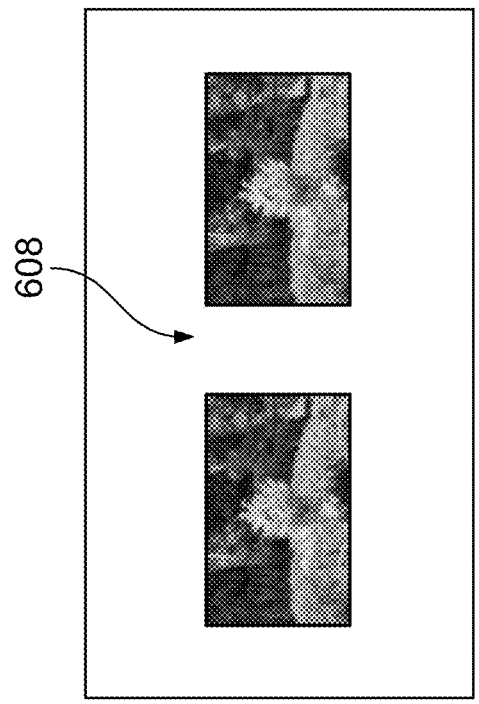
FIG. 9C is a view of the images of the garden of FIG. 9B after adjusting the relative position of the displays, in accordance with some embodiments of the present specification.
Figure 9B:
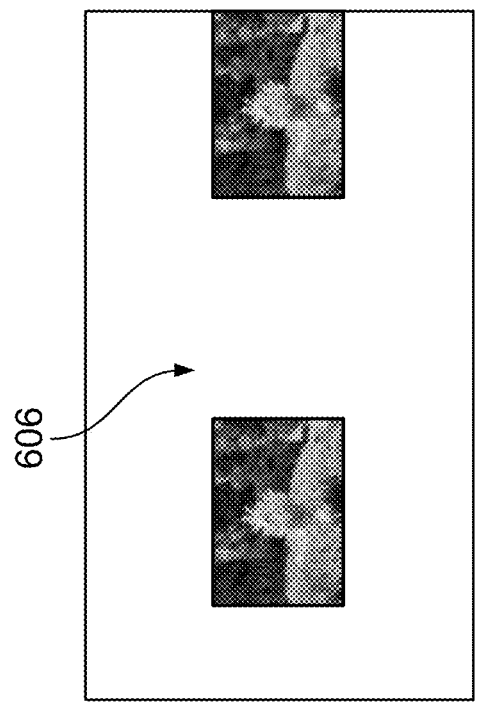
FIG. 9B illustrates images of a garden that may be viewed by a user before adjusting for interpupillary distance, in accordance with some embodiments of the present specification.

FIG. 6A illustrates an exemplary image that may be used to align the user's eye separation. It should be appreciated that the visual images shown in FIG. 9A are generated by the software platform, as described above, and presented in one or more of the above-mentioned displays. It should further be appreciated that the system 100 generates one or more prompts, and receives one or more user inputs, using the above-described hardware.

Referring to FIG. 6A, a horizontal line 602 is presented to one eye of the user, and a vertical line 604 is presented to the other eye. A user, while looking at the two lines, is unable to view the vertical line 604 at the center of the horizontal line 602 because of that user's specific IPD. A user then modulates one or more input devices to cause the vertical line 604 to be positioned at the center of the horizontal line 602. The image may be moved by any number of input mechanisms, including toggling a physical wheel, pressing an icon, receiving a voice command, among other approaches, to cause the visual display to adjust the pixel coordinates of the images such that they appear to move further together or apart relative to each other. Therefore, the relative position of the displays viewed by the user are displaced and/or adjusted till the vertical line 604 appears at the center of the horizontal line 602. In some embodiments, a horizontal line is used over a vertical line to gain perspective. In alternative embodiments, other images than the horizontal 602 and vertical 604 lines are used to adjust the displays for IPD users.

FIG. 6B illustrates images 606 of a garden that may be viewed by a user before adjusting for user's IPD, in accordance with some embodiments of the present specification. FIG. 6C is a view of the images 608 of the same garden after adjusting the relative position of the displays, in accordance with some embodiments of the present specification. Thus, the present specification provides an objective way to move images to fit naturally positioned eyes. In an embodiment, the vision enhancement system of the present specification may be used for providing lateral phoria correction. Accordingly, in one embodiment, the IPD mode enables a user to view a vertical line perpendicular to a horizontal line and use an input mechanism to align the vertical line to a center of the horizontal line. Preferably, upon centering the vertical line along the length of the horizontal line, the system visually indicates the centering having occurred and transitions the user out of IPD mode or provides the user with an option to manually transition out of IPD mode.

Embodiments of the present specification may provide additional assistive modes of operating the vision enhancement system 100. Such modes may include and are not limited to a mode for transforming physical text into images where the text is electronically re-generated as black letters on a white background or inverted white letters on a black background, transforming physical text into electronically re-generated images in which each text line is magnified one line at the center of an image of a page, or transforming physical text into images where the text is electronically re-generated as lettering on a green or yellow background. Such modes may further include a mode for Optical Character Recognition (OCR) where the vision enhancement system 100 converts text to voice so as to read out image of a page or any other text, a mode of taking a snapshot of a viewed image, and a mode for streaming media such as from Netflix or any other media service. The user may switch between different assistive modes with the aid of a button or any other type of interface provided with the system 100.

Visual Field Measurement

Figure 9F:
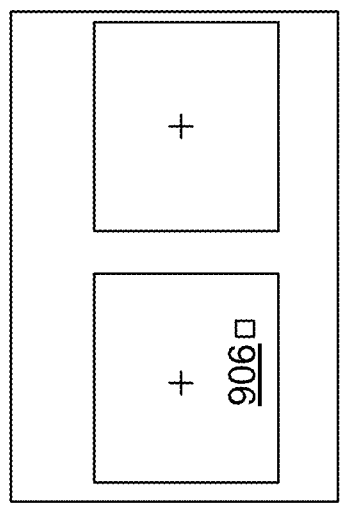
FIG. 9F illustrates yet another target point displayed to the user, in accordance with some embodiments of the present specification.
Figure 9E:
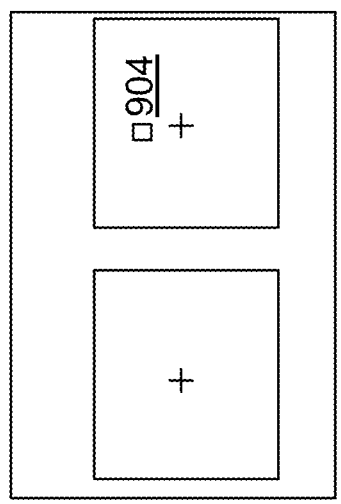
FIG. 9E illustrates another target point, in accordance with some embodiments of the present specification.
Figure 9D:
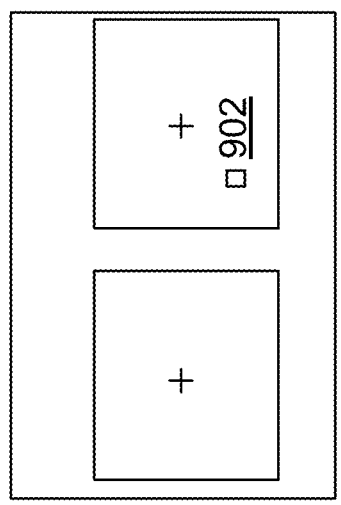
FIG. 9D illustrates a target point that is displayed to a user, in accordance with some embodiments of the present specification.

In the visual field measurement diagnostic mode, a user's visual field is evaluated to identify areas within the user's visual field where the user may experience "holes" or the inability to receive or process visual information, also referred to as scotoma. In some embodiments, the vision enhancement system measures a user's visual field using Humphrey-like measurements. Accordingly, in embodiments, the system 100 generates, and present through a display, a random sequence of points, representing small targets, in the visual field of the user, while the user fixates vision at a central point in the field. The system 100 instructs the user that, every time the user sees a target, the user acknowledges its visibility by pressing a button or otherwise interacting with an interface provided with the system 100. In case the user is unable to see a target, system 100 continues to display the target for a specified period of time before flashing the next target point. The area in the visual field of the user, where the previously flashed target was not acknowledged by the user, is noted as a possible area where the user's vision is either blurred or missing. FIGS. 9D, 9E, and 9F illustrate images from an exemplary sequence that is displayed to a user to determine the areas of scotomas, in accordance with some embodiments of the present specification. Referring to FIG. 9D, a target point 902 is displayed to a user. FIG. 9E illustrates another target point 904. FIG. 9F illustrates yet another target point 906, displayed to the user. The errors that the user makes during the test are recorded on the device and a graph showing the deficits (scotomas) is made available.

With the option to diagnose the scotomas, the user is able to autonomously determine areas in his or her visual field where the user's vision is poor or non-existent. In embodiments, the methods of the present specification may be used to perform static threshold perimetry (and in an embodiment, using Humphrey standards) for measuring the visual field of a patient. In embodiments, the methods of the present specification may be used to perform kinetic perimetry, such as by using Goldmann standards, for measuring the visual field of a user.

Therapeutic Mode

One of the therapeutic modes that are provided by some of the embodiments in accordance with the present specification, include a therapy for improving strabismus. Strabismus is a condition where visual axes of both the eyes of an individual are not parallel, so that the eyes appear to be looking in different directions. Therapeutic exercises may improve this condition over a period of time with regular practice. The objective of such exercises is to retrain the neuro-muscular pathway in the affected eye so as to strengthen it and align it in its natural position, parallel to the other eye. The vision enhancement system 100 generates and displays therapeutic exercises to the user with the advantage that the user may perform the exercises while the user is mobile, and while viewing a scene from the real environment instead of a synthetic scene, therefore making the training process more enjoyable and comfortable.

In embodiments, the system 100 displays an image in alignment with the eccentric eye. At this position the user, who normally has double vision, would see a merged or fused world with the images from the two eyes aligned. Then, the user or a clinician, either manually or according to a prearranged program, can begin to shift the image corresponding to the eccentric eye back to a more central position, therefore coaxing the user to re-align the eccentric eye.

Figure 10A:
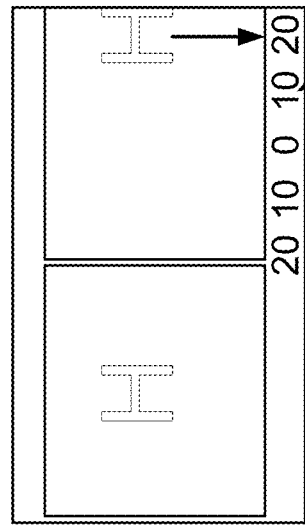
FIG. 10A illustrates an embodiment of the present specification where the letter H, when in alignment with the eccentric eye on the right, is at a scale of 20.
Figure 10B:
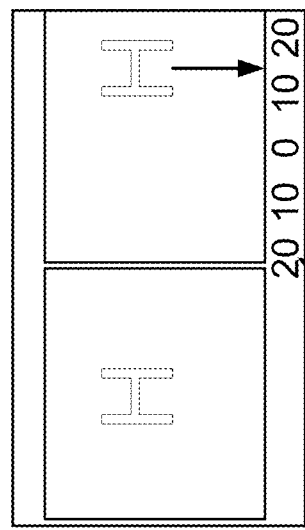
FIG. 10B illustrates an embodiment of the present specification where the letter is moved to a scale between 10 and 20.
Figure 10C:
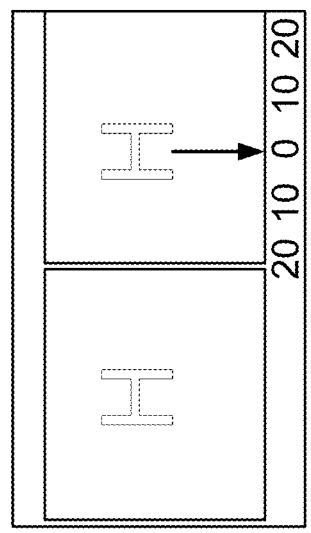
FIG. 10C illustrates an embodiment of the present specification where the letter is at a central position.

FIGS. 10A, 10B, and 10C illustrate an exemplary sequence from a training session using a letter H displayed to the user, in accordance with some embodiments of the present specification. FIG. 10A illustrates an initial position of letter H, aligned with the two eyes in their respective fields of view. The image includes an exemplary slider 1002 to observe the extent of repositioning of the eye. In FIG. 10A, the letter H, when in alignment with the eccentric eye on the right, is at a scale of 20. The letter is gradually moved towards a more central position in the user's field of view. In FIG. 10B, the letter is moved to a scale between 10 and 20. In FIG. 10C, the letter is at a central position. In embodiments, the letter is moved gradually, in a manner that the user does not realize the act of exercising while performing it. Further, in embodiments, the user is presented with images from a real scene that is captured by the camera of vision enhancement system 100 and displayed to the user through its display. Over a period of time, the user is able to strengthen the neuromuscular pathway while improving the native alignment of the eccentric eye.

More specifically, the at least one processor of the vision enhancement system is configured to first position a first image along the right eye's visual axis and position a second image along the left eye's visual axis where a visual axis is a line representing a direction of gaze. In individuals with strabismus, the visual axes of the left eye and the right eye are not parallel, indicating that the direction of gaze is offset from center for one eye greater than for the other eye. Over a predefined period of time, the at least one processor moves at least one of the first image or second image such that a) the visual axes extending through the images relative to the eyes become more and more parallel over the predefined period of time and b) the offset from center of the visual axes extending through the images become closer and closer in value over the predefined period of time. The progression of the visual axes toward being parallel and being equally offset from center happens gradually over time and, when achieved, the at least one processor terminates the process. The period of time may be over a week, a month, six months, a year, or any day increment therein.

Although the various embodiments of the present specification have been described with particular focus on a user autonomously using the vision enhancement system 100, the present specification is also designed for use for clinicians, doctors, family members, or other medical and care persons, who may be remotely located from the user. The system 100 may communicate with a computing device to exchange vision-related data processed by the system, in addition to reproducing video data on a remote display, such as the one illustrated and described in context of FIG. 1D.

The above examples are merely illustrative of the many applications of the system of present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A computer readable non-transitory medium comprising a plurality of executable programmatic instructions adapted to be executed in a portable user vision enhancement and/or assessment system, wherein the portable user vision enhancement and/or assessment system comprises a housing adapted to fit onto a user's head, a memory physically coupled to the housing, a display physically coupled to the housing, a camera physically coupled to the housing, adapted to view a scene in front of the user, and configured to obtain input video images of the scene, and at least one processor physically coupled to the housing and in data communication with the memory, display, and camera, wherein, when executed by the at least one processor, the plurality of executable programmatic instructions is adapted to:

generate data representative of a first graphical user interface; and cause said data to be transmitted to the display, wherein, when displayed on the display, the first graphical user interface comprises:

a first option that, when actuated by the user, causes the plurality of executable programmatic instructions to generate a plurality of assistive operational modes;

a second option that, when actuated by the user, causes the plurality of executable programmatic instructions to generate a plurality of therapeutic operational modes; and a third option that, when actuated by the user, causes the plurality of executable programmatic instructions to generate a plurality of diagnostic modes, wherein the plurality of executable programmatic instructions, when executed by the at least one processor, is further configured to receive a selection from the user of one of the assistive operational modes, therapeutic operational modes, or diagnostic operational modes, to access a portion of the plurality of executable programmatic instructions associated with the selection, and to execute the portion of the plurality of executable programmatic instructions associated with the selection.

2. The computer readable non-transitory medium of claim 1, wherein, when executed by the at least one processor, the plurality of executable programmatic instructions is further adapted to concurrently present the first option, the second option, and the third option in the first graphical user interface.

3. The computer readable non-transitory medium of claim 1, wherein, the plurality of assistive operational modes comprises at least one of a magnification mode, a magnification mode with a customizable bubble, a retinitis pigmentosa mode, or a contrast sensitivity mode and wherein an option for selecting each of the plurality of assistive operational modes is concurrently displayed in a same graphical user interface.

4. The computer readable non-transitory medium of claim 1, wherein, the plurality of diagnostic operational modes comprises at least one of an interpupillary distance mode or a visual field measurement mode and wherein an option for selecting each of the plurality of diagnostic operational modes is concurrently displayed in a same graphical user interface.

5. The computer readable non-transitory medium of claim 1, wherein, the plurality of therapeutic operational modes comprises a strabismus treatment mode.

6. The computer readable non-transitory medium of claim 1, wherein, upon the first option being actuated by the user, the plurality of executable programmatic instructions is further adapted to cause the at least one processor to generate data representative of a second graphical user interface and cause the at least one processor to transmit said data representative of the second graphical user interface to the display and wherein, when displayed on the display, the second graphical user interface displays at least one of a magnification mode option, a magnification with a bubble mode option, a retinitis pigmentosa mode option or a contrast sensitivity mode option.

7. The computer readable non-transitory medium of claim 6, wherein, upon the retinitis pigmentosa mode option being selected by the user, the plurality of executable programmatic instructions is further adapted to cause the at least one processor to access a portion of the plurality of executable programmatic instructions associated with the retinitis pigmentosa mode and wherein, upon executing the portion of the plurality of executable programmatic instructions associated with the retinitis pigmentosa mode, the plurality of executable programmatic instructions is further adapted to cause the at least one processor to access images of the scene encompassing a first field of view and minimize all content in said images to fit within a second field of view that is smaller than the first field of view.

8. The computer readable non-transitory medium of claim 6, wherein, upon the contrast sensitivity mode option being selected by the user, the plurality of executable programmatic instructions is further adapted to cause the at least one processor to access a portion of the plurality of executable programmatic instructions associated with the contrast sensitivity mode and wherein, upon executing the portion of the plurality of executable programmatic instructions associated with the contrast sensitivity mode, the plurality of executable programmatic instructions is further adapted to cause the at least one processor to access images of the scene and processes the images to preferentially enhance the images at a spatial frequency Cp, where Cp is the maximum spatial frequency at which a user can discern contrast.

9. The computer readable non-transitory medium of claim 6, wherein, upon the contrast sensitivity mode option being selected by the user, the plurality of executable programmatic instructions is further adapted to cause the at least one processor to access a portion of the plurality of executable programmatic instructions associated with the contrast sensitivity mode and wherein, upon executing the portion of the plurality of executable programmatic instructions associated with the contrast sensitivity mode, the plurality of executable programmatic instructions is further adapted to cause the at least one processor to acquire images of the scene, access stored frequencies indicative of the user's contrast sensitivity, adjust frequencies of the images of the scene based upon the stored frequencies, and generate images having adjusted frequencies for display.

10. The computer readable non-transitory medium of claim 6, wherein, upon the magnification mode option being selected by the user, the plurality of executable programmatic instructions is further adapted to cause the at least one processor to access a portion of the plurality of executable programmatic instructions associated with the magnification mode and wherein, upon executing the portion of the plurality of executable programmatic instructions associated with the magnification mode, the plurality of executable programmatic instructions is further adapted to cause the at least one processor to access images of the scene and process the images to generate a magnification region in the images, wherein the magnification region has a magnification level that has a higher magnification level near a center of the magnification region and a lower magnification level near an edge of the magnification region.

11. The computer readable non-transitory medium of claim 6, wherein the plurality of executable programmatic instructions is further adapted to cause the at least one processor to access a portion of the plurality of executable programmatic instructions associated with the contrast sensitivity mode and wherein, upon executing the portion of the plurality of executable programmatic instructions associated with the contrast sensitivity mode, the plurality of executable programmatic instructions is further adapted to cause the at least one processor to determine frequencies within a spatial range at which the user experiences contrast sensitivity and to adjust one or more of the images to compensate for the determined frequencies.

12. The computer readable non-transitory medium of claim 1, wherein, upon the second option being actuated by the user, the plurality of executable programmatic instructions is further adapted to cause the at least one processor to generate data representative of a second graphical user interface and transmit said data representative of the second graphical user interface to the display and wherein, when displayed on the display, the second graphical user interface displays at least one of an interpupillary distance mode or a visual field measurement mode.

13. The computer readable non-transitory medium of claim 12, wherein, upon the interpupillary distance mode option being selected by the user, the plurality of executable programmatic instructions is further adapted to cause the at least one processor to access a portion of the plurality of executable programmatic instructions associated with the interpupillary distance mode and wherein, upon executing the portion of the plurality of executable programmatic instructions associated with the interpupillary distance mode, the plurality of executable programmatic instructions is further adapted to cause the at least one processor to generate a vertical line and a horizontal line perpendicular to the horizontal line and, in response to a user input, move the vertical line along a length of the horizontal line.

14. The computer readable non-transitory medium of claim 12, wherein, upon the visual field measurement mode option being selected by the user, the plurality of executable programmatic instructions is further adapted to cause the at least one processor to access a portion of the plurality of executable programmatic instructions associated with the visual field measurement mode and wherein, upon executing the portion of the plurality of executable programmatic instructions associated with the visual field measurement mode, the plurality of executable programmatic instructions is further adapted to cause the at least one processor to a) generate, and cause a display of, a sequence of targets to the user, b), record data representative of the user having seen a first of the targets in response to the user's input, cause the first of the targets to disappear and cause a display of a second of the targets, c) continue to display each of the targets for a predefined period of time and, in an absence of the user's input, record a lack of response, with the predefined period of time, and d) generate data representative of the user's visual field and indicate where, within the user's visual field, the user is unable to see based on b and c.

15. The computer readable non-transitory medium of claim 1, wherein, upon the third option being actuated by the user, the plurality of executable programmatic instructions is further adapted to cause the at least one processor to generate data representative of a second graphical user interface and transmit said data representative of the second graphical user interface to the display and wherein, when displayed on the display, the second graphical user interface displays a strabismus treatment mode.

16. The computer readable non-transitory medium of claim 15, wherein, upon the strabismus treatment mode option being selected by the user, the plurality of executable programmatic instructions is further adapted to cause the at least one processor to access a portion of the plurality of executable programmatic instructions associated with the strabismus treatment mode and wherein, upon executing the portion of the plurality of executable programmatic instructions associated with the strabismus treatment mode, the plurality of executable programmatic instructions is further adapted to cause the at least one processor to position a first image along a first visual axis associated with the user's right eye and position a second image along a second visual axis associated with the user's left eye and, over a predefined period of time, move the first image relative to the second image.

17. The computer readable non-transitory medium of claim 16, wherein, upon the strabismus treatment mode option being selected by the user, the plurality of executable programmatic instructions is further adapted to cause the at least one processor to access a portion of the plurality of executable programmatic instructions associated with the strabismus treatment mode and wherein, upon executing the portion of the plurality of executable programmatic instructions associated with the strabismus treatment mode, the plurality of executable programmatic instructions is further adapted to cause the at least one processor to continue to position the first image along the first visual axis relative to the second image along the second visual axis until the first visual axis is parallel to the second visual axis.

18. The computer readable non-transitory medium of claim 16, wherein, upon the strabismus treatment mode option being selected by the user, the plurality of executable programmatic instructions is further adapted to cause the at least one processor to access a portion of the plurality of executable programmatic instructions associated with the strabismus treatment mode and wherein, upon executing the portion of the plurality of executable programmatic instructions associated with the strabismus treatment mode, the plurality of executable programmatic instructions is further adapted to cause the at least one processor to continue to position the first image along the first visual axis relative to the second image along the second visual axis until the first visual axis is offset from a center point of the user's field of view by a first amount and the second visual axis is offset from the center point of the user's field of view by a second amount, wherein the first amount is equal to the second amount.

19. The computer readable non-transitory medium of claim 16, wherein the period of time ranges from one week to one year.

20. The computer readable non-transitory medium of claim 1, wherein the plurality of executable programmatic instructions are adapted to be executed in a mobile phone and wherein the display, camera, and at least one processor is positioned in the mobile phone.

21. The computer readable non-transitory medium of claim 1, wherein the plurality of executable programmatic instructions are adapted to be executed in a virtual reality headset and wherein the display, camera, and at least one processor is positioned in the virtual reality headset.

* * * * *